(12) United States Patent
Shin et al.

(10) Patent No.: US 9,645,135 B2
(45) Date of Patent: May 9, 2017

(54) NANOWIRE FIELD-EFFECT TRANSISTOR BIOSENSOR WITH IMPROVED SENSITIVITY

(75) Inventors: Kyeong-Sik Shin, Los Angeles, CA (US); Chi On Chui, Encino, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 13/991,413

(22) PCT Filed: Dec. 2, 2011

(86) PCT No.: PCT/US2011/063157
§ 371 (c)(1),
(2), (4) Date: Aug. 19, 2013

(87) PCT Pub. No.: WO2012/075445
PCT Pub. Date: Jun. 7, 2012

(65) Prior Publication Data
US 2013/0337567 A1 Dec. 19, 2013

Related U.S. Application Data

(60) Provisional application No. 61/419,434, filed on Dec. 3, 2010, provisional application No. 61/494,373, filed on Jun. 7, 2011.

(51) Int. Cl.
*H01L 29/78* (2006.01)
*G01N 33/50* (2006.01)
(Continued)

(52) U.S. Cl.
CPC .............. *G01N 33/50* (2013.01); *B82Y 15/00* (2013.01); *G01N 27/4146* (2013.01); *H01L 29/78* (2013.01); *Y10T 436/143333* (2015.01)

(58) Field of Classification Search
CPC ........ H01L 29/78; B82Y 15/00; G01N 33/50; G01N 27/4146
(Continued)

(56) References Cited

U.S. PATENT DOCUMENTS 6,482,639 B2 11/2002 Snow et al.
2003/0089899 A1* 5/2003 Lieber et al. .............. 257/9
(Continued)

FOREIGN PATENT DOCUMENTS

CN 100345280 C 10/2007
WO WO-02/01647 A1 1/2002
WO WO-02/48701 A2 6/2002

OTHER PUBLICATIONS

Cui et al., "Nanowire Nanosensors for Highly Sensitive and Selective Detection of Biological and Chemical Species", Science, vol. 293, pp. 1289-1292 (2001).
(Continued)

*Primary Examiner* — Rebecca M Fritchman
(74) *Attorney, Agent, or Firm* — Foley & Lardner LLP; Cliff Z. Liu

(57) ABSTRACT

The present invention is directed to a multiwire nanowire field effect transistor (nwFET) device for the measurement. The device includes a sensing nanowire having a first end and a second end and a nanowire FET having a first end and a second end, wherein the first end of the sensing nanowire is connected to the nanowire FET to form a node. Additionally, the first end of the nanowire FET is connected to a source electrode, the second end of the nanowire FET is connected to a drain electrode, and the second end of the sensing nanowire is connected to a base electrode. The sensing nanowire is derivatized with a plurality of immobilized capture probes that are specific for a target(s) of interest. The device is used to detect biomolecules or to detect the change in the ionic environment of a sample. In
(Continued)

a further embodiment, the sensing nanowire is derivatized with amino, carboxyl or hydroxyl groups. Upon a change in ionic environment, or binding of a molecule to the sensing nanowire, the sensing nanowire current ($I_B$) fluctuates. This fluctuation is amplified and readout as the nanowire FET drain current ($I_D$). Accordingly, the present invention provides for label-free detection of biomolecules and may find use as a point-of-care diagnostic device.

31 Claims, 20 Drawing Sheets

(51) Int. Cl.
    *G01N 27/414*     (2006.01)
    *B82Y 15/00*     (2011.01)

(58) Field of Classification Search
    USPC .............................. 436/63, 94, 149; 257/24
    See application file for complete search history.

(56) References Cited

U.S. PATENT DOCUMENTS

| | | | |
|---|---|---|---|
| 2004/0173815 A1 | 9/2004 | Yeo et al. | |
| 2006/0246497 A1* | 11/2006 | Huang et al. | 435/6 |
| 2007/0238186 A1* | 10/2007 | Sun et al. | 436/94 |
| 2009/0057762 A1* | 3/2009 | Bangsaruntip et al. | 257/347 |
| 2009/0142558 A1* | 6/2009 | Jiao | B82Y 30/00 |
| | | | 428/206 |
| 2010/0050745 A1 | 3/2010 | Liu et al. | |
| 2010/0052014 A1* | 3/2010 | Matsushita | H01L 29/7787 |
| | | | 257/192 |
| 2010/0059736 A1* | 3/2010 | Tombler, Jr. | B82Y 10/00 |
| | | | 257/14 |

OTHER PUBLICATIONS

Streifer, J.A. et al., "Covalent Functionalization and Bimolecular Recognition Properties of DNA-Modified Silicon Nanowires," Nanotechnology, (2005), vol. 16, pp. 1868-1873.
Extended European Search Report for European application No. 11845848.8 dated Dec. 18, 2014.
First Office Action and Search Report for Chinese application No. 201180066619.7 dated Jun. 19, 2014 (English translation of search report).
Second Office Action dated Apr. 29, 2015 for Chinese Application No. 20118066619.7, 4 pages.
English Translation of Third Chinese Office Action dated Oct. 23, 2015, from related Chinese patent application No. 201180066619.7.
Third Chinese Office Action dated Oct. 23, 2015, from related Chinese patent application No. 201180066619.7.
Fourth Office Action for Chinese Patent Application No. 201180066619.7 dated Mar. 28, 2016.
International Search Report for International Application No. PCT/2011/063157 mailed Jul. 27, 2012.
Shin et al., "Novel T-Channel Nanowire FET with Built-in Signal Amplification for pH Sensing," Electron Devices Meeting (IEDM), 2009 IEEE International Meeting, Dec. 2009, pp. 1-4.
Shin et al., "Schottky Contacted Nanowire Field-Effect Sensing Device With Intrinsic Amplification," IEEE Electron Device Letters, vol. 31, No. 11, Nov. 2010, pp. 1317-1319.

* cited by examiner

SEQUENCE LISTING

```
<160> NUMBER OF SEQ ID NOS: 4

<210> SEQ ID NO 1
<211> LENGTH: 17
<212> TYPE: DNA
<213> ORGANISM: Influenza A virus
<220> FEATURE:
<221> NAME/KEY: misc_feature
<222> LOCATION: (1)..(17)
<223> OTHER INFORMATION: Peptide nucleic acid

<400> SEQUENCE: 1
tcactgcaaa ctcatgg                                                  17

<210> SEQ ID NO 2
<211> LENGTH: 17
<212> TYPE: DNA
<213> ORGANISM: Influenza A virus
<220> FEATURE:
<221> NAME/KEY: misc_feature
<222> LOCATION: (1)..(17)
<223> OTHER INFORMATION: Peptide nucleic acid

<400> SEQUENCE: 2
agaaggccaa tccagtc                                                  17

<210> SEQ ID NO 3
<211> LENGTH: 50
<212> TYPE: DNA
<213> ORGANISM: Influenza A virus
<220> FEATURE:
<221> NAME/KEY: misc_feature
<222> LOCATION: (1)..(50)
<223> OTHER INFORMATION: Peptide nucleic acid
<220> FEATURE:
<221> NAME/KEY: misc_feature
<222> LOCATION: (34)..(34)
<223> OTHER INFORMATION: n may be inosine

<400> SEQUENCE: 3
atgtaggacc atgagtttgc agtgagtaga aggncacatt ctggattgcc              50

<210> SEQ ID NO 4
<211> LENGTH: 50
<212> TYPE: DNA
<213> ORGANISM: Influenza A virus
<220> FEATURE:
<221> NAME/KEY: misc_feature
<222> LOCATION: (1)..(50)
<223> OTHER INFORMATION: Peptide nucleic acid

<400> SEQUENCE: 4
gaggtcattg actggattgg ccttctccac tatgtaagac cattccggca              50
```

NANOWIRE FIELD-EFFECT TRANSISTOR BIOSENSOR WITH IMPROVED SENSITIVITY

CROSS-REFERENCE TO RELATED APPLICATIONS

This application claims the benefit under 35 U.S.C. §119 (e) of U.S. Provisional Application Ser. No. 61/419,434, filed Dec. 3, 2010, and U.S. Provisional Application Ser. No. 61/494,373, filed Jun. 7, 2011, both of which are incorporated by reference in their entireties for all purposes.

SEQUENCE LISTING

The instant application contains a Sequence Listing which has been submitted in ASCII format via EFS-Web and is hereby incorporated by reference in its entirety. Said ASCII copy, created on Aug. 19, 2013, is named 102352-0300_SL.txt and is 1,398 bytes in size.

BACKGROUND OF THE INVENTION

Real-time and label-free sensing of charged biomolecules, chemicals and ions is useful in many applications such as toxin detection, disease diagnosis, and drug screening. For highly specific biomolecular detection, various optical sensing approaches have been developed that are categorized as either fluorescence-based detection or label-free detection. Although fluorescence-based detection permits, in some instances, a sensitivity down to a single molecule, an imprecise number of fluorophores per molecule limits the quantitative nature of these assays. Label-free optical methods including refractive index change, optical absorption, and Raman spectroscopic detection are relatively simple but are hampered by scalability and sensitivity.

Highly sensitive MEMS-based mechanical biosensors have been investigated that employ either an optical or electrical detection scheme to track the cantilever displacement upon specific binding between the biofunctionalized receptor layer and target molecules. However, to increase sensitivity, the cantilever dimension must be reduced into the nanoscale which in turn compromises the viability of optical detection due to diffraction during the tip focusing. Although integrated piezoresistive cantilever biosensors eliminate an optical detection component, the inherent detection of the quasi-static surface-layer by these devices induced stress, and, prevents these devices from tracking the stochastic nature of affinity-based interactions, which is on the order of nanoseconds or microseconds. This limitation is especially true when the target molecule is in the presence of many weakly bound species.

Quasi-1-D semiconductor nanowires are uniquely suitable for high sensitivity label-free detection applications. Their microscale to nanoscale volumes and large surface to volume ratio are respectively favorable for bulk detection, e.g., radiation, and surface sensing, for example, to detect biochemical molecules. Semiconductor nanowires have previously been configured as substrate-gated FET channels. Exposed Si nanowires atop an insulator layer have exhibited a limit of detection (LOD) of <100 fM for immunoglobulins and ~10 fM for DNA. These sensing nanowires have also been integrated into detection systems with microfluidic modules.

SUMMARY OF THE INVENTION

For integrated sensing systems employment, silicon nanowire field effect transistors (Si nwFETs) are particularly attractive due to their scalability and good sensitivity. A common disadvantage of conventional nwFETs is the low level of output signal which hinders the ultimate performance of the devices. The present invention addresses this and other needs.

In one aspect, the present invention is directed to a multiwire nanowire field effect transistor (nwFET) device. In one embodiment, the device comprises a sensing nanowire having a first end and a second end and a nanowire FET having a first end and a second end, wherein the first end of the sensing nanowire is connected to the nanowire FET to form a node. The sensing nanowire and nanowire FET each comprise at least one semiconductor material. Additionally, the first end of the nanowire FET is connected to a source electrode, the second end of the nanowire FET is connected to a drain electrode, and the second end of the sensing nanowire is connected to a base electrode. In a further embodiment, the first end of the sensing nanowire is connected to the nanowire FET at an angle between about 10° and 170°.

The sensing nanowire, in one embodiment, is derivatized with a plurality of immobilized capture probes that are specific for a target(s) of interest. In a further embodiment, the sensing nanowire is derivatized with free amino groups. A change in pH of a solution introduced onto the device alters the charges on amino groups, and therefore, alters the electrical properties of the sensing nanowire, e.g., conductance. The signal from the sensing nanowire is amplified by the nanowire FET to allow for greater sensitivity.

In another embodiment, the nwFET device comprises a sensing nanowire having a first end and a second end and a nanowire FET having a first end and a second end, and the first end of the sensing nanowire is connected to the nanowire FET at about a 90° angle, to form a node, thereby creating a T-shape structure. The first and second ends of the sensing nanowire, in one embodiment, are in the same plane as the first and second ends of the nanowire FET. In another embodiment, the second end of the sensing nanowire is in a different plane than the first and second ends of the nanowire FET.

In one embodiment, a multiwire nanowire field effect transistor (nwFET) device is provided. The device comprises a sensing nanowire having a first end and a second end and a nanowire FET having a first end and a second end, wherein the first end of the sensing nanowire is connected to the nanowire FET to form a node, the first end of the nanowire FET is connected to a source electrode, the second end of the nanowire FET is connected to a drain electrode, and the second end of the sensing nanowire is connected to a base electrode. The sensing nanowire and nanowire FET each comprise at least one semiconductor material. In a further embodiment, the first end of the sensing nanowire is connected to the nanowire FET at an angle between about 10° and about 170°. In a further embodiment, the nanowires are fabricated on a silicon substrate, for example, on silicon oxide. In even a further embodiment, the sensing nanowire and the nanowire FET have about one or more of the same dimensions (e.g., about the same height, width, aspect ratio and/or length).

In another aspect, the nanowire FET sensor provided herein is used as a biosensor. For example, in one embodiment, the sensing nanowire is derivatized with a plurality of immobilized capture probes, either directly, or through the use of linker molecules. In one embodiment, the immobilized capture probes are homogeneous, i.e., each probe is specific for the same target. In another embodiment, the immobilized capture probes are heterogeneous, i.e., at least a first capture probe is specific for a first target and at least a second capture probe is specific for a second target.

The immobilized capture probe, in one embodiment, is part of a specific binding pair. A test sample, which may or may not comprise the specific binding partner (i.e., target molecule) for the immobilized capture probe, is introduced onto the device. In one embodiment, the sample is an electrolyte solution, blood specimen or cell lysate. In another embodiment, the sample is a physiological sample, and undergoes some processing (e.g., PCR) prior to introduction onto the device. If the sample includes the target molecule, it will bind to the device, and a change in various electrical quantities such as current, capacitance and resistance is induced. In one embodiment, a change in the nwFET drain current is readout to determine if a binding event has occurred.

In one aspect, the present invention provides a novel nwFET sensor structure with a T-shape channel (T-nwFET) to introduce a built-in, transistor-like signal amplification mechanism. By designing the nanowire resistances and voltage biases, any fluctuation in the sensing nanowire current ($I_B$) upon a sensing event is intimately amplified and readout as the nanowire FET drain current ($I_D$). In one embodiment, multiple devices are cascaded together to obtain multiple stages of signal amplification. In other words, the signal from a first device is amplified by the nwFET of a second device to generate an amplified second signal. If a third device is cascaded, the second signal from the second device is amplified by the nwFET of a third device to generate an amplified third signal. Accordingly, in one embodiment, the present invention provides a plurality of nwFET devices connected in series. In a further embodiment, the plurality of devices includes two, three, four or five devices.

In one embodiment, the devices provided herein are fabricated by top-down nanofabrication. The Schottky junction scheme substantially lowers the fabrication thermal budget and eliminates any complex dopant junction engineering.

In another aspect, a method for detecting the change in pH in a sample is provided. In one embodiment, the method comprises measuring the baseline drain current ($I_D$) associated with a nwFET device comprising a sensing nanowire having a first end and a second end and a nanowire FET having a first end and a second end, wherein the first end of the sensing nanowire is connected to the nanowire FET at an angle between about 10° and 170°, to form a node. The first end of the nanowire FET is connected to a source electrode, the second end of the nanowire FET is connected to a drain electrode, and the second end of the sensing nanowire is connected to a base electrode. The sensing nanowire is derivatized with free amino groups. The method further comprises introducing a test sample onto the sensing nanowire, and measuring the change in $I_D$ after introduction of the sample, wherein a change in $I_D$ is associated with a change in pH of the test sample.

In yet another aspect, a method for detecting the presence or absence of a molecule in a sample is provided. In one embodiment, the method comprises measuring the baseline drain current ($I_D$) associated with a nwFET device comprising a sensing nanowire having a first end and a second end and a nanowire FET having a first end and a second end, wherein the sensing nanowire and nanowire FET each comprise at least one semiconductor material, the first end of the sensing nanowire is connected to the nanowire FET to form a node. The first end of the nanowire FET is connected to a source electrode, the second end of the nanowire FET is connected to a drain electrode, and the second end of the sensing nanowire is connected to a base electrode. The sensing nanowire is derivatized with a plurality of immobilized capture probes that are specific for a target(s) (analyte) of interest. The method further comprises introducing a test sample onto the sensing nanowire and measuring the change in $I_D$ after introduction of the sample, wherein a change in $I_D$ is associated with the target (analyte) of interest binding the device. In a further embodiment, the first end of the sensing nanowire is connected to the nanowire FET to form a node at an angle between about 10° and 170°.

BRIEF DESCRIPTION OF THE FIGURES

FIG. 1 (right) is a drawing of a multiplanar nwFET architecture.

FIG. 10, right, is a graph showing the change in drain current as a function of sensing gate voltage (i.e., sensing gate biasing).

FIG. 11, right, is a graph showing the change in amplification ratio as a function of sensing gate current extracted at $V_D=1$ V, $V_S=0$ V, and $V_{SG}=3V$.

FIG. 13 (right) is a graph showing real-time pH sensing measurement by a T-nwFET of the present invention. Sensing gate current and drain current are provided as a function of time.

DETAILED DESCRIPTION OF THE INVENTION

Figure 1:
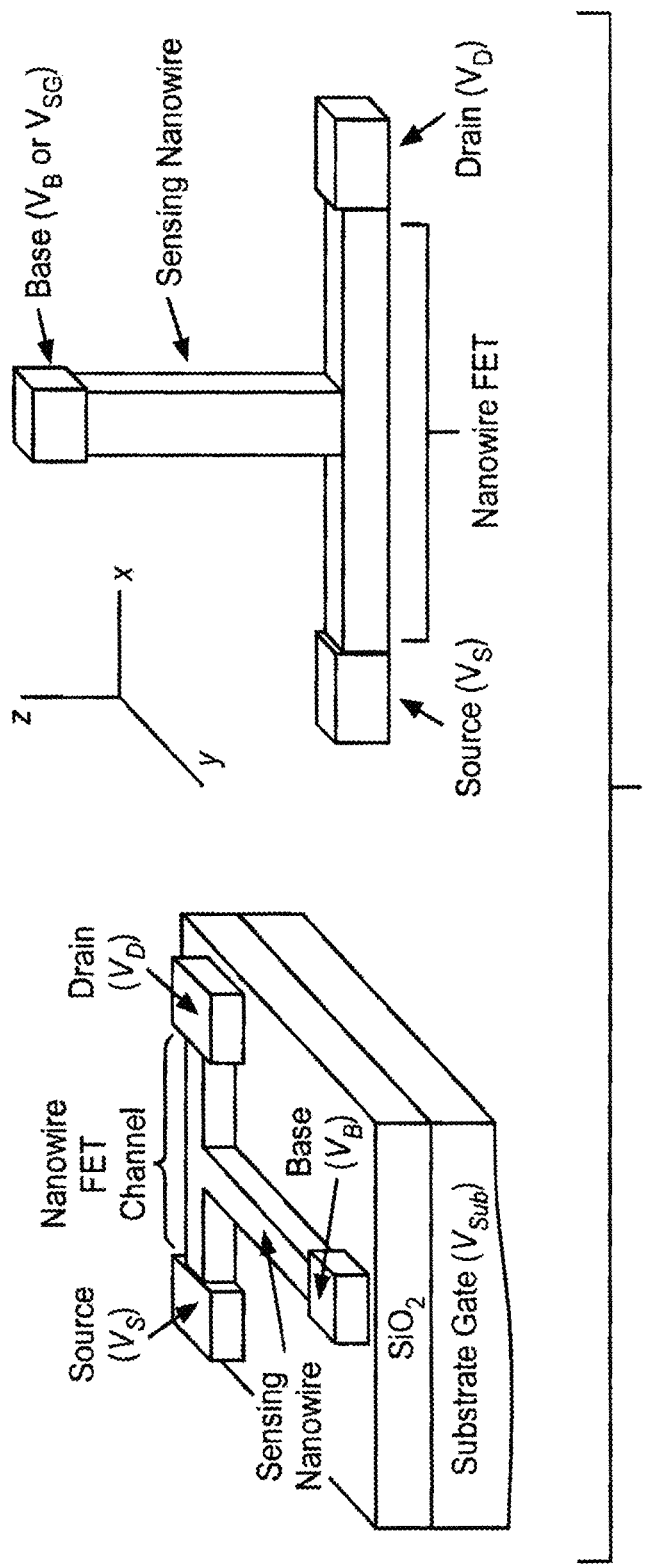
FIG. 1 (left) is a drawing of a T-nwFET of the present invention.
Figure 2:
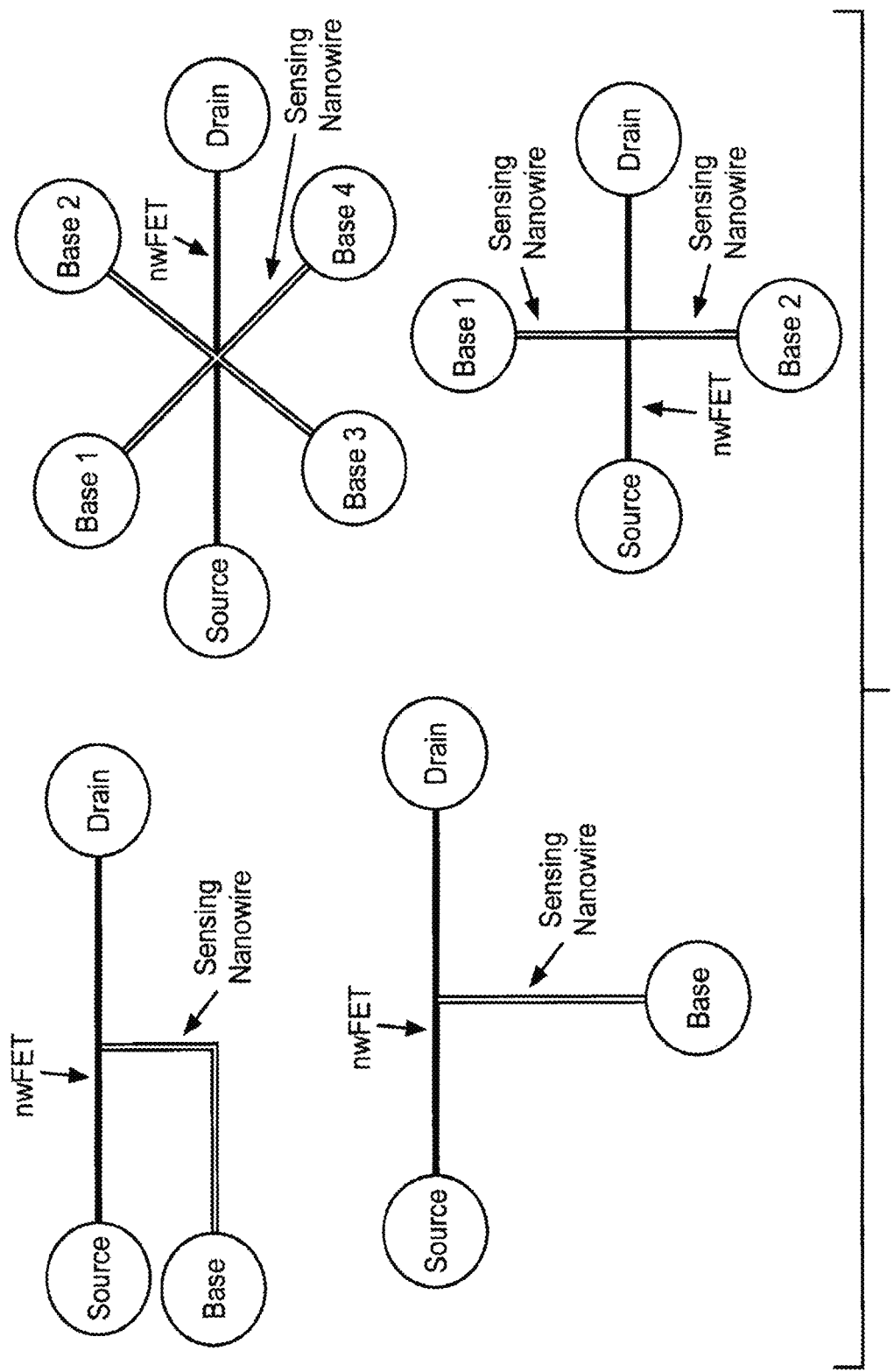
FIG. 2 are drawings of various nwFET device architectures for use with the present invention.

In one aspect, the present invention provides a nanowire FET device with a built-in signal amplification mechanism for chemical and biomedical sensing applications, including point-of-care (POC) diagnostic applications (FIGS. 1 and 2). The nanowire FET sensors provided herein are comprised of one or more semiconductor materials, and permit visual-label-free and real-time electronic detections of charged biomolecules with specificity and sensitivity. The high surface detection sensitivity arises from the inherently large surface area-to-volume ratio of the quasi-one-dimensional nanowires. The charge-to-current signal transduction occurs at a front-end nanowire FET which thereby minimizes parasitics and thus noise. This scheme additionally requires no imaging equipments and the sensors themselves are readily interfaced and integrated with readout electronics.

Figure 3:
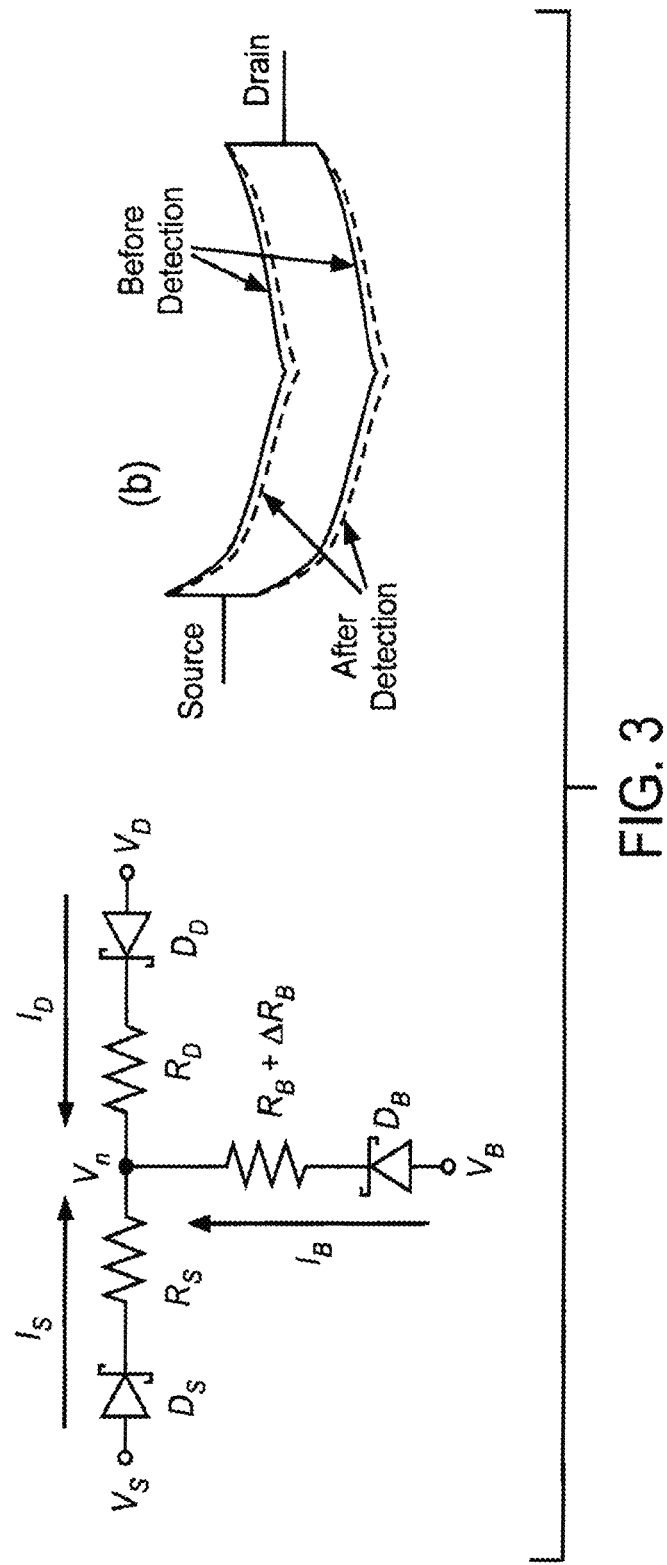
FIG. 3 is a circuit diagram corresponding to the T-nwFET device and an energy band diagram extracted at $V_{DS}=V_{Sub-S}=2V$ along the nwFET channel with a $V_B=4V$.

By designing the nanowire resistances and voltage biases, as provided below, any fluctuation in the sensing nanowire current ($I_B$) upon a sensing event is intimately amplified and readout as the nanowire FET drain current ($I_D$) (FIG. 3). Accordingly, harnessing the same large surface area-to-volume ratio advantage, the nanowire-based sensing device provided herein increases detection sensitivity through a built-in amplification mechanism with minimal noise.

Figure 4:
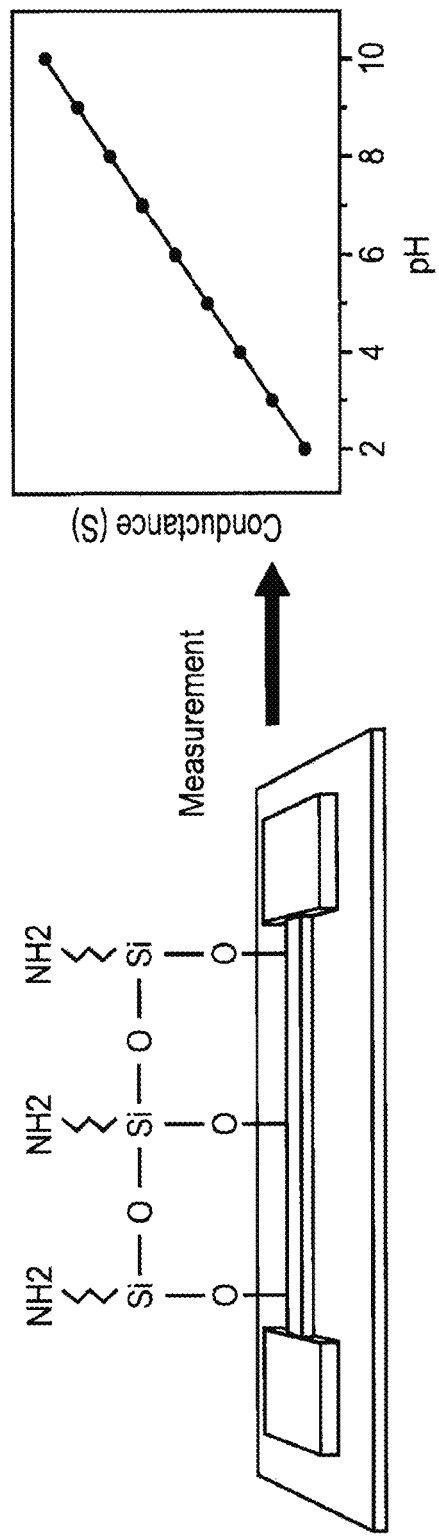
FIG. 4 shows a diagram of an exposed, functionalized channel of a nanowire FET (left). Variation in pH can be determined by monitoring the channel's conductance (right).
Figure 6:
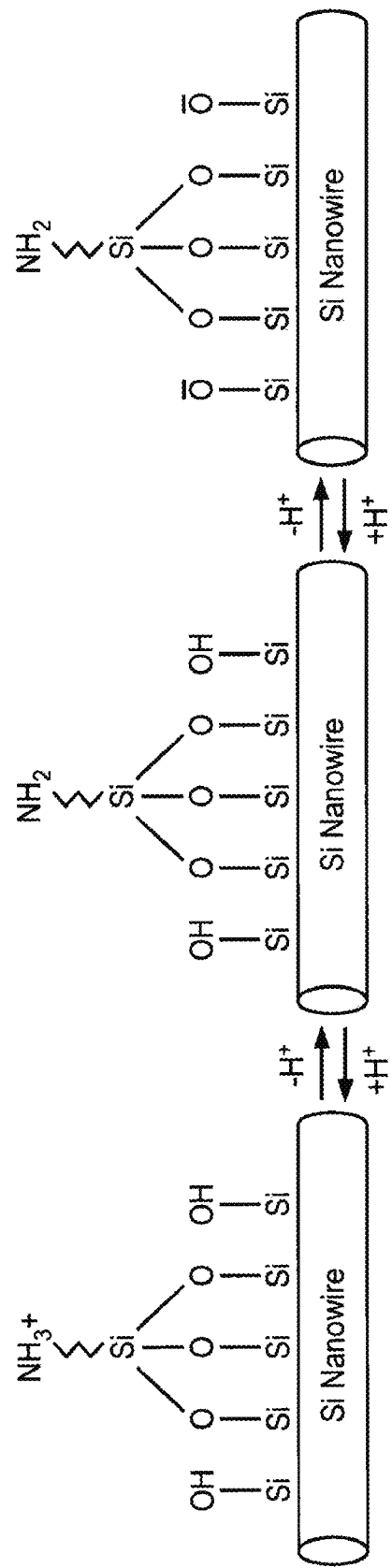
FIG. 6 is a drawing showing the principle of pH sensing with —$NH_2$ functionalized Si nanowire FET. Left movement in Fig. corresponds to protonation due to pH reduction, which induces positive charges. Deprotonation induces negative charges (right movement).

In some embodiments, the nanowire FET device is in the shape of a T, with a sensing nanowire orthogonal to a nanowire FET (nwFET) (FIG. 1). However, other configurations of the two wires are amenable for use in the present invention (FIG. 2). The nanowire FET device provided herein is applicable to a multitude of label-free sensing and detection assays, as described in further detail below. For example, in one embodiment, the devices provided herein are used to detect the presence or absence of one or more target molecules in suspension or solution, for example, the presence or absence of one or more proteins or nucleic acids. In another embodiment, the devices provided herein are used to detect changes in pH in a solution (FIGS. 4 and 6). In yet another embodiment, the devices provided herein monitor the concentration of one or more physiological ions such as sodium ($Na^+$), potassium ($K^+$), calcium ($Ca^{2+}$), magnesium ($Mg^{2+}$), chloride ($Cl^-$), hydrogen phosphate ($HPO_4^{2-}$), and hydrogen carbonate ($HCO_3^-$). In this embodiment, the sensing nanowire is exposed to an electrolyte solution and a change in ion concentration in the solution results in a fluctuation in the sensing nanowire current ($I_B$). This fluctuation is amplified and readout as the nanowire FET drain current ($I_D$).

In one embodiment, the devices of the present invention achieve at least about a 10×, or at least about 20× or at least about 50× increase in pH detection sensitivity, or physiological ion sensitivity, over a conventional one-nanowire FET sensor.

Device Architecture and Operation

In one embodiment, the present invention is directed to a nanofabricated sensor structure comprising a sensing nanowire and a nanowire field-effect transistor (nwFET) and, each having a first end and a second end. Each nanowire comprises a semiconductor material, and in one embodiment, the semiconductor material is the same for each wire. Therefore, in this embodiment, the multiwire portion of the device is monolithic. The nanowires, in one embodiment, are fabricated from a semiconductor substrate. In one embodiment, the substrate is a doped semiconductor substrate.

The sensing nanowire, in one embodiment, is used to detect changes in the environment, for example, pH changes in a solution. In another embodiment, the sensing nanowire is derivatized with immobilized capture probes, which are designed to bind target molecules in a test sample. Binding events cause a fluctuation in the sensing nanowire current ($I_B$). This fluctuation is amplified and readout as the nanowire FET drain current ($I_D$). In one embodiment, multiple devices are cascaded together to obtain multiple stages of signal amplification. In other words, the signal from a first device is amplified by the nwFET of a second device to generate an amplified second signal. If a third device is cascaded, the second signal from the second device is amplified by the nwFET of a third device to generate an amplified third signal. Accordingly, in one embodiment, the present invention provides a plurality of nwFET devices connected in series. In a further embodiment, the plurality of devices includes two, three, four or five devices.

From a general biosensor functionality standpoint, the interface between the biomolecular receptor (e.g., immobilized capture probes, immobilized amino groups) and signal transducer (sensing nanowire) should be designed to minimize the inherent electrical interference that may compromise the detection sensitivity. This issue is further substantiated if the interface is in turn connected to a remote amplifier or impedance converter via long electrical leads. According to these criteria, the FET biosensor structure with an insulator interface between the biological environment and electronic device constitutes amongst the most elegant interfaces because the biomolecular signal transduction occurs at the sensor front-end.

In order to detect biomolecules with low concentration and specifically, and to allow for single molecule resolution, the nanowire FET biosensor output signals need to be amplified. One issue with extrinsic amplification is the added parasitics, which thus degrades the overall performance of the device. It is therefore highly desirable to bring the amplifying stage closest to the transduction front-end to boost the detection sensitivity with reduced noise contribution. The devices provided herein accomplish this goal by coupling a nanowire FET with the sensing nanowire.

The nanowire FET is connected to a source electrode at its first end and connected to a drain electrode at its second end. The first end of the sensing nanowire intersects with the nanowire FET to form a node, and the second end of the sensing nanowire is connected to a base electrode (also referred to herein as "SG" or "sensing gate" electrode). The voltage associated with the source electrode is referred to as $V_S$, the voltage associated with the drain electrode is referred to as $V_D$ and the voltage associated with the base electrode is referred to as $V_B$ or $V_{SG}$.

In one embodiment, the sensitivity of the device to be tunable. In one embodiment, the sensitivity is tuned by modifying the dimensions and/or structure of the nanowire device. For example, in one embodiment, the aspect ratio of one or both of the wires is altered, or the width or length of one or both of the wires is altered. One of ordinary skill in the art will recognize that the nanowire dimensions cannot be adjusted in a post-fabrication manner.

In one embodiment, to increase its signal level as the back-gate nwFET channel, the sensing nanowire is either be shortened or repeated in parallel. However, this also increases the device footprint and may only enhance the signal-to noise ratio slightly. The present invention, in one embodiment, is directed to a nwFET device comprising at least two, at least three, or at least four sensing nanowires, each having a first end and a second end, wherein the first ends of the sensing nanowires are connected to the FET nanowire at individual nodes in between the nanowire FET's first and second ends. The second end of each sensing nanowire has a base electrode associated with it, which has a corresponding voltage of $V_B$. In one embodiment, each sensing nanowire comprises the same immobilized capture probes. In another embodiment, at least two of the sensing nanowires have different immobilized capture probes, to allow for detection of multiple analytes.

In another embodiment, the tunability in sensitivity is obtained by voltage biasing on the nanowire FET device.

As provided above, the nanowire device provided herein integrates a sensing nanowire and a nanowire field effect transistor to form a multiwire structure. In one embodiment, the first end of the sensing nanowire is connected to the nanowire FET (nwFET) at a node in between the nanowire FET's first and second end. The intersection point or node of the two wires, in one embodiment, is about an equal distance from the first end and the second end of the nwFET. However, the intersection point (node) of the two wires can be at any point between the first and second ends of the nanowire FET. In one embodiment, the nwFET has a length from the first end to the second end equal to X, and the node is present between about 0.01X and about 0.99X. In another embodiment, the nwFET has a length from the first end to the second end equal to X, and the node is present between about 0.1X and about 0.9X. In yet another embodiment, the nwFET has a length from the first end to the second end equal to X, and the node is present between about 0.3X and about 0.7X. In one embodiment, the nwFET has a length from the first end to the second end equal to X, and the node is present at about 0.05X, at about 0.1X, at about 0.2X, at about 0.3X, at about 0.4X, at about 0.5X, at about 0.6X, at about 0.7X, at about 0.8X, at about 0.9X or at about 0.95X.

The devices of the invention, in one embodiment, comprise at least one sensing nanowire having a first end and a second end. The first end of the sensing nanowire connects with the nanowire FET to form a node, and the second end of the sensing nanowire is connected to a base electrode (FIGS. 1 and 2). As provided above, the at least one sensing nanowire and nanowire FET each comprise at least one semiconductor material. The at least one sensing nanowire, in one embodiment, is a straight nanowire, curved nanowire, serpentine nanowire, or in the shape of an "L". These shapes are defined by the lithographical process, as described below. Various architectures of the nwFET devices of the invention are provided in FIGS. 1 and 2. In one embodiment, the device of the invention comprises at least two sensing nanowires, and the two sensing nanowires are connected to the nwFET at the same node. In another embodiment, the device of the invention comprises at least two sensing nanowires, and the two sensing nanowires are connected to the nwFET at different nodes.

The length of either the at least one sensing nanowire or the nwFET, in one embodiment, is defined as the shortest distance between the first end and the second end of the respective nanowire. In one embodiment, the length of the sensing nanowire and/or the nwFET is in the range of about 20 nm to about 30 μm. In one embodiment, the length of the at least one sensing nanowire and the nwFET is independently about 20 nm, about 30 nm, about 40 nm, 50 nm, about 60 nm, about 70 nm, about 80 nm, about 90 nm, about 100 nm, about 110 nm, about 120 nm, about 150 nm and about 200 nm, about 500 nm, about 1 μm, about 2 μm, about 3 μm, about 4 μm, about 5 μm, about 10 μm, about 20 μM, or about 30 μm. In one embodiment, the lengths of the sensing nanowire and the nanowire FET are the same. In another embodiment, the lengths of the sensing nanowire and the nanowire FET are different.

In one embodiment, the sensing nanowire intersects the nanowire FET at about a 90° angle (i.e., the sensing nanowire is orthogonal to the nanowire FET), forming a "T-shaped" configuration (FIG. 1). Although the multiwire devices provided herein are generally referred to as "T-shaped" or "T-channel" FETs, the device is not limited to an orthogonal architecture. As used herein, a T-shaped or T-channel device includes any devices where the sensing nanowire intersects the nanowire FET at some angle between about 10° and about 170°, for example, an angle between about 30° and about 150°, or an angle between about 50° and about 100°. In one embodiment, the angle is measured using the following three points: (1) the first end of the FET to (2) the node of the FET-sensing nanowire to (3) the second end of the sensing nanowire.

In one embodiment, the sensing nanowire intersects the nanowire FET at about 10°, about 20°, about 30°, about 35°, about 40°, about 45°, about 50°, about 55°, about 60°, about 65°, about 70°, about 75°, about 80°, about 85° or about 90°.

In one embodiment, the first and second ends of the nanowire FET and the first and second ends of the sensing nanowire are present in the same plane (FIG. 1, left). This type of device is fabricated using top-down nanolithography techniques known to those of ordinary skill in the art. For example, a negative photoresist, in one embodiment, is spun onto a semiconductor substrate (e.g., silicon), and developed to define the nanowire structures (i.e., in this embodiment, the nanowires comprise silicon as the semiconductor material). The semiconductor substrate can be provided as a doped substrate. Each nanowire has about the same height, as the photoresist is applied to the semiconductor substrate as a uniform layer. Width of the nanowires will vary somewhat depending on mask resolution, whether the photoresist exposure to the electron beam (or ultraviolet light) is uniform and whether exposure to the photoresist developer is uniform.

The nwFET devices provided herein is not limited to planar devices (FIG. 1, right). For example, the nwFET device can be fabricated in a multi-step process, thereby forming a multi-planar device (FIG. 1, right). Accordingly, in one embodiment, the first and second ends of the nanowire FET are in a different plane than the second end of the sensing nanowire. In one embodiment, such a device is fabricated by two lithography and etching steps. The first step, in one embodiment, defines the vertical fin with the foot print of the bottom nanowire FET. The second step patterns the vertical fin into a vertical pillar to form the sensing nanowire.

In another embodiment, the device provided herein is in the form of a vertical semiconductor pillar (sensing nanowire channel) synthesized above a planar bulk FET channel.

In one embodiment, the device of the present invention has a plurality of sensing nanowires, each having a first and second end, and a single nwFET channel having a first end and a second end. Each sensing nanowire has a base electrode associated with its second end. The first end of each sensing nanowire forms a node between the first and second of the nwFET channel. Additionally, the first end of the nwFET is connected to a source electrode and the second end of the nwFET is connected to a drain electrode. Accordingly, devices in the shape of a cross or plus or asterisk are within the scope of the invention.

As provided above, the multiwire nanowire device (T-nwFET) of the present invention comprises a sensing nanowire and a nanowire FET, each comprising a semiconductor material. The semiconductor material, in one embodiment, is initially present as a semiconductor substrate, used for fabrication of the device. The semiconductor material, in one embodiment, comprises a doped semiconductor material. In one embodiment, each wire comprises the same semiconductor material, thereby forming a monolithic nanowire structure. In one embodiment, the nanowires are comprised of silicon. However, other semiconductor materials are amenable for use in the present invention. For example, in one embodiment, each nanowire independently comprises a group IV semiconductor material, a group III-V semiconductor material, a group II-VI semiconductor material, a group I-VII semiconductor material, a group IV-VI semiconductor material, a group IV-VI semiconductor material, a group V-VI semiconductor material, a group II-V semiconductor material, an oxide semiconductor material, a metal oxide semiconductor material, an organic semiconductor material, a composite semiconductor material, a doped semiconductor material or a layered semiconductor material.

The sensing nanowire and the nanowire FET can have the same, about the same, similar, or different dimensions, for example, the same, about the same, or different heights, width, diameter, length and/or aspect ratios.

The intrinsic amplification mechanism of the novel sensor can be understood with the help of the equivalent circuit illustrated in FIG. 3. The node potential at the intersection between the two wires is labeled as $V_n$, and each nanowire segment from this node to the respective electrode is represented as an ideal Schottky diode in series with the nanowire resistance. The sensing nanowire and FET drain current are related to the electrode potentials (e.g., $V_B$ and $V_D$) by $$I_B = I_0\left[\exp\left(\frac{q((V_B - V_n) - I_B(R_B + \Delta R_B))}{(k_B T)}\right) - 1\right] \quad (1)$$

$$I_D = I_0\left[\exp\left(\frac{q((V_D - V_n) - I_D R_D)}{(k_B T)}\right) - 1\right] \quad (2)$$

$$I_0 = AA^{**}T^2 \exp\left(-\frac{q\phi B_p}{k_B T}\right) \quad (3)$$

where A, A**, $k_B$, $\Phi_{Bp}$, q, $R_B$, $\Delta R_B$, $R_D$, and T are, respectively, the diode area, effective Richardson constant, Boltzmann constant, Schottky barrier height, electronic charge, sensing nanowire resistance, change in $R_B$ due to sensing, drain nanowire resistance, and absolute temperature. By eliminating $V_n$ from (1) and (2), $I_D$ can be related to $I_B$, an equation that has to be solved by iteration. The current amplification ratio ($dI_D/dI_B$) can, thus, be computed numerically. In one embodiment, identical Schottky contacts are used, and therefore, the amplification ratio is determined by the nanowire resistances $R_B$ and $R_D$ and potentials $V_D$ and $V_B$. In other words, the desirable amplification can be tuned by the nanowire geometry during structural design and/or voltage biasing during sensing operation.

In one embodiment, the T-nwFET operations depend on the biasing voltage combination. Moreover, the achievable intrinsic amplification is also determined by the structure, geometry, and dimensions of the device.

Figure 5:
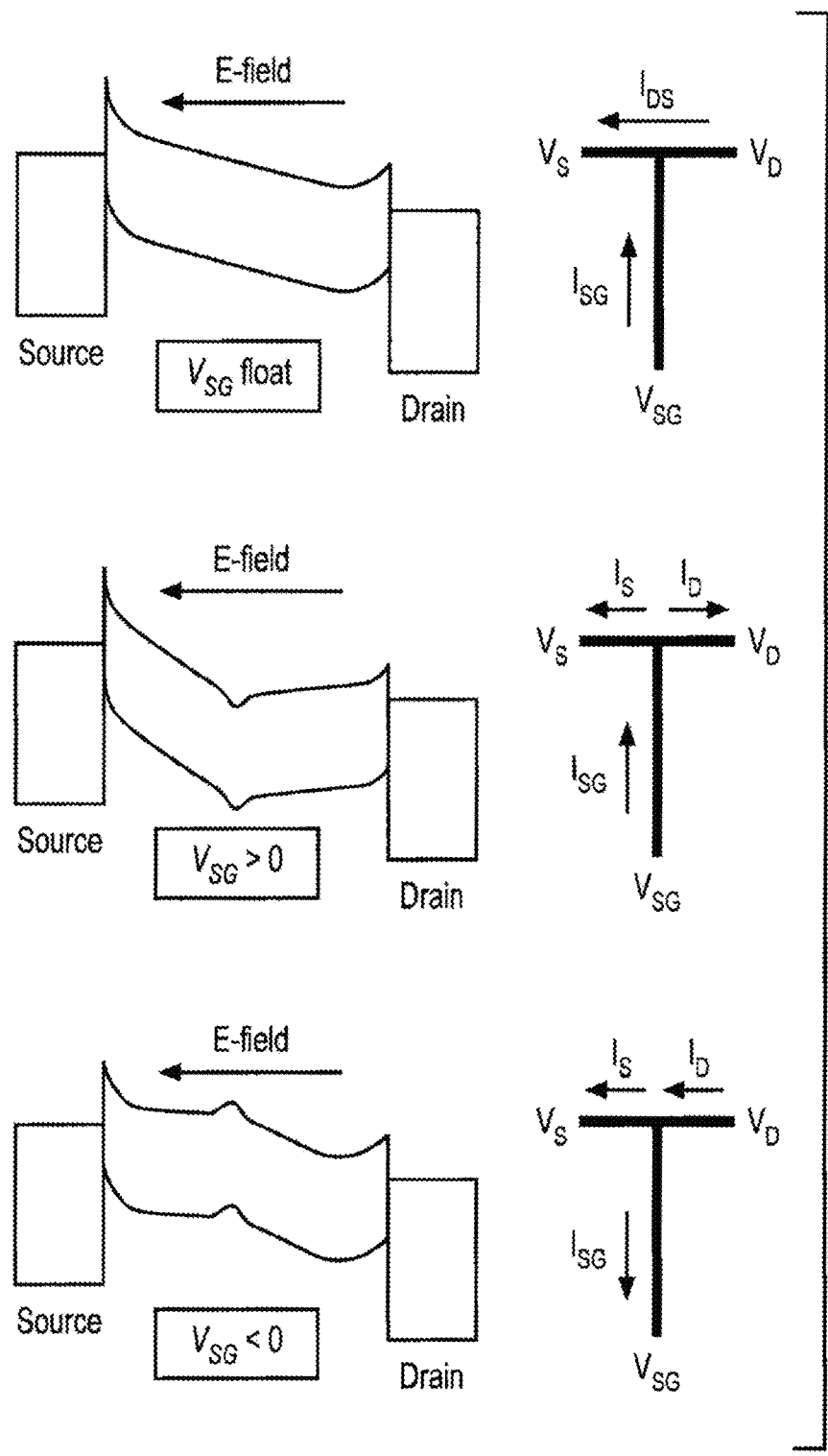
FIG. 5 are energy band diagrams between source and drain (along the nwFET channel), and the respective current flow directions under different sensing gate biases (with $V_D>0$ $V_{SG}>0$).

During the sensing operation, both the drain ($V_D$) and base ($V_B$) contacts are biased positively against the source contact. The modulation of sensing nanowire conductance due to specific binding of target biomolecules yields a non-zero $\Delta R_B$ value and thus changes the $I_B$ according to Equation (1). That in turn varies the potential $V_n$ and modifies the energy band profile between the source and drain contacts (FIG. 5). The resultant change in the voltage difference ($V_D-V_n$) causes an exponential change in $I_D$ such that a modest amplification of the detected signal is achieved.

Three dimensional semiconductor device simulations have been carried out (FIG. 7) to validate the anticipated operating and amplification mechanism of the proposed sensing device. The extracted energy band profile (FIG. 7) closely resembles that shown in FIG. 5.

In some embodiments, there is a need to consider and mitigate the electric field screening of the bound target molecule charges by counter ions in the electrolyte solution (e.g., test sample). This effect, commonly known as the Debye-Hückel screening, is common in solution samples with high background ionic strength like the physiological fluids. Although electronic detections of charged biomolecules in such circumstances may still be accomplished, the detected signal level is in most cases, too low to be differentiated from background levels.

Figure 7:
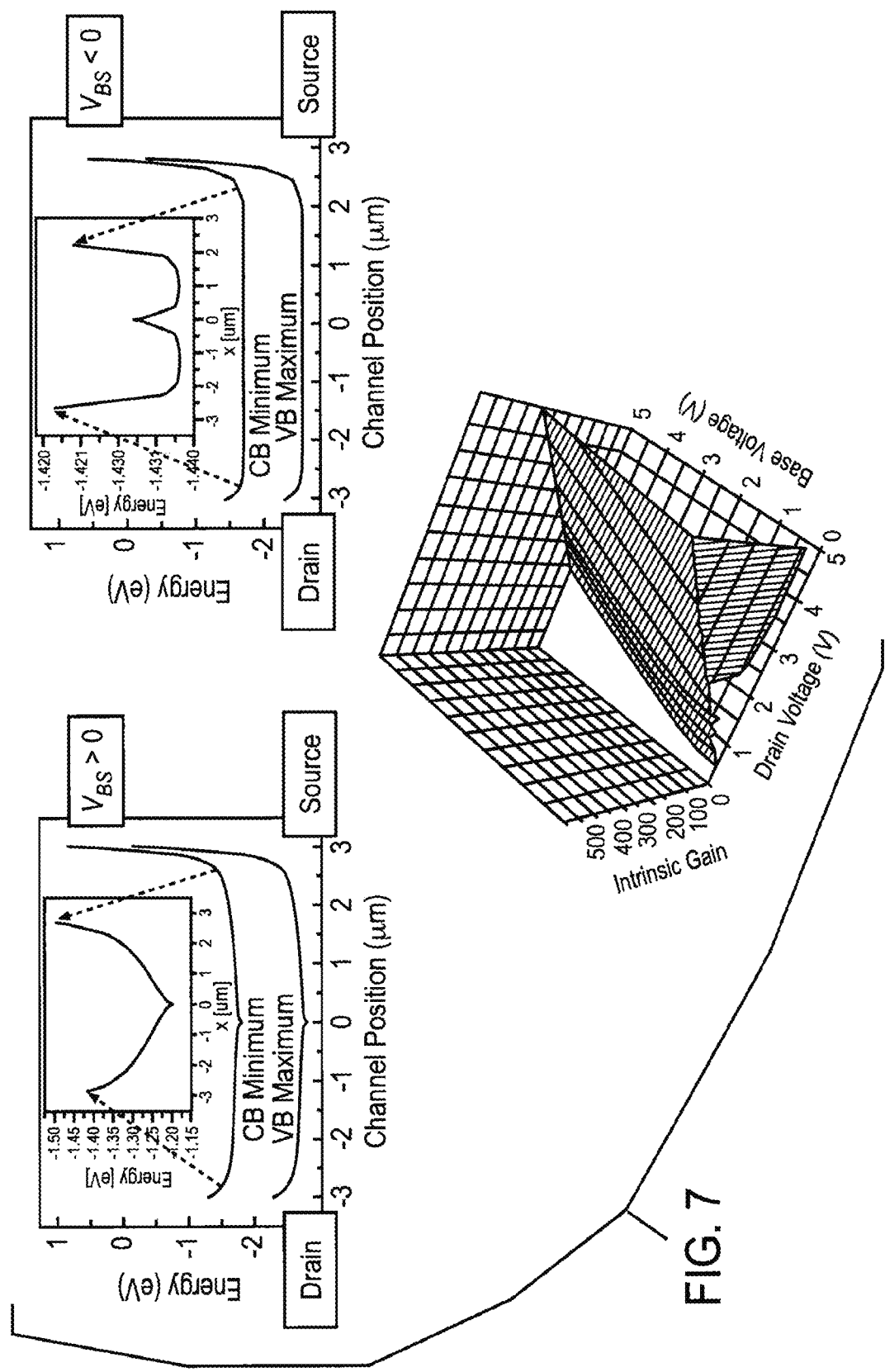
FIG. 7 are graphs showing device simulation results with Sentarus. Generated 3D T-nwFET simulation structure. Energy band diagrams extracted at $V_{DS}=V_{Sub-S}=2V$ along the nwFET channel with a $V_{SG}=4V$ (top left) and $V_{SG}=-4V$ (top right). The bottom graph shows intrinsic amplification of the device as a function of drain and base voltages.

In one embodiment, a de-screening voltage biasing method is carried out that permits charge detection at a distance much longer than the counter ion Debye screening length. Detection is permitted because under high electric field in the solution, the relative speed between the charged biomolecule and counter ions is so high that the counter ions cannot relax (or respond) fast enough to form a complete screening layer. This phenomenon has been examined to explain the measured Wien Effect. Similar to the Possion-Nernst-Plank modeling approach, the same de-screening simulation capability has been implemented in the theoretical analysis provided herein. As illustrated in FIG. 7, the simulated electrostatic potential profiles in the ionic solution can be extended far away from the charged molecule under appropriate external biases $V_B$ to reduce electrostatic screening.

Figure 8:
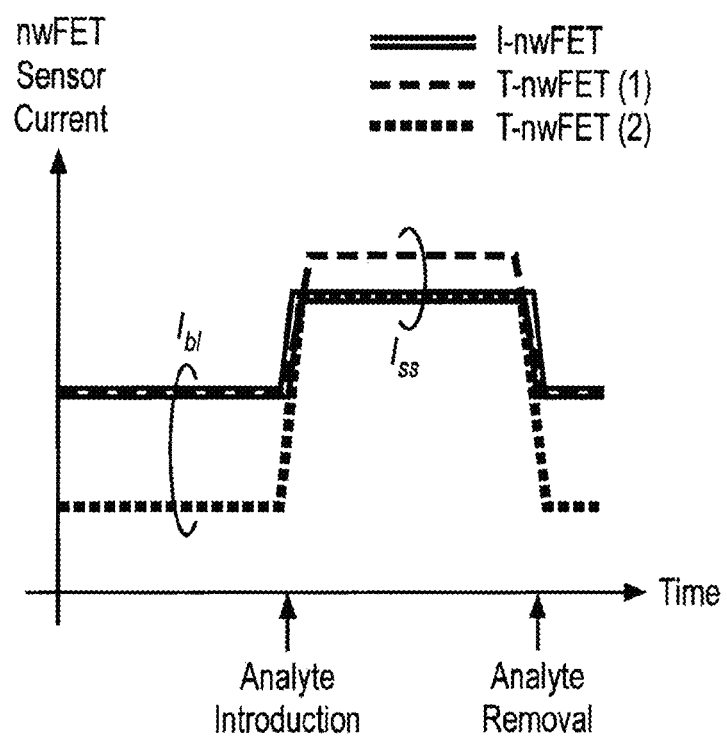
FIG. 8 is a graph showing generated current as a function of analyte introduction and removal for both the multiwire device of the invention (T-nwFET) and a single wire nwFET (I-nwFET).

Compared to the generic single wire nwFET sensors, the sensitivity advantage in the devices of the invention (T-nwFET sensors) is manifested in at least one of two ways. On one hand, a larger detected biomarker signal can be obtained ($I_{detected}$) with the same mean blank signal level ($I_{blank}$) (FIG. 8). Alternatively, the mean $I_{blank}$ can be lowered with about the same $I_{detected}$ value by applying different biasing voltages (FIG. 8). Since the noise of $I_{blank}$ scales with the $I_{blank}$ itself, an $I_{blank}$ reduction will in turn lower both the level of detection and level of detection and limit of quantification. Therefore, in one embodiment, the devices provided herein allow for detection of target molecules in a test sample, present at a concentration of greater than or equal to about 1 fM. This allows for detection of target molecules in limited sample volume, for example, samples from children or infants.

Device Fabrication

While conventional Si nwFETs can be fabricated using either the top down or bottom-up method with some tradeoffs (Table 1), a common disadvantage of the bottom up approach is the low level of output signal that hinders their ultimate performance.

TABLE 1

Comparison of Si nwFETs made with different methods

| Method | Advantage | Disadvantage |
| --- | --- | --- |
| Top down | CMOS compatible processing Flexibility in changing channel shape | High surface defect Low level signal |
| Bottom up | Low surface defect | Positioning problem Low level signal |

A schematic of one embodiment of a Si T-nwFET is provided in FIG. 1. The Si T-nwFETs devices provided herein are designed and fabricated using the top-down method. The device's dopant free structure with Schottky source and drain junctions simplify the fabrication process and reduce the thermal budget. As described below, the architecture of the device provides a higher sensitivity in biological sensing, for example in pH detection, compared to the single nanowire nwFET.

As provided above, the sensing nanowire and nanowire FET of the device each comprises a semiconductor material. In one embodiment, the T-nwFET sensor devices are fabricated on oriented silicon-on-insulator (SOI) substrates made by separation by implanted oxygen process. In another embodiment, the substrate is a bonded SOI substrate. However, other semiconductor substrates may be used to fabricate the devices provided herein, to provide nanowires comprising a semiconductor material. In another embodiment, a non-semiconductor substrate (e.g., a handle wafer) is used to fabricate the device. In this embodiment, a semiconductor material is present on the surface of the substrate so that the wire(s) eventually include the material.

In one embodiment, Group IV, III-V, II-VI, I-VII, IV-VI, IV-VI, V-VI, II-V semiconductor materials, oxides, organic semiconductor materials, layered semiconductor materials, doped semiconductor materials, or a combination thereof, can be used as the device substrate, a portion of the substrate (e.g., a layered substrate or individual wires having a different substrate) or can be present on the surface of a substrate. Substrates are available commercially as wafers, and a plurality of devices can be fabricated from each wafer.

In one embodiment, a semiconductor wafer substrate is used to fabricate a plurality of nwFET devices of the invention, and at least two of the devices are designed and fabricated to detect different target molecules (e.g., a viral antigen, enzyme or antibody). For example, in one embodiment, the wafer comprises a plurality of devices and at least one of the plurality of devices includes a sensing nanowire comprising immobilized capture probes specific for H1N1 influenza virus and at least one of the plurality of devices includes a sensing nanowire comprising immobilized capture probes specific for H5N1 influenza virus.

In one embodiment, the nwFET device substrate comprises silicon, silicon oxide, interconnection metals such as titanium, platinum, aluminum, or gold, or a combination thereof. In a further embodiment, the substrate is a multi-layer substrate, as known to those of ordinary skill in the art. It is desirable that a substrate is robust to allow for multiuse of the device.

The starting semiconductor layer, in one embodiment, ranges from about 5 nm to about 500 nm in thickness. For example, the semiconductor layer has a thickness of about 5 nm, about 10 nm, about 50 nm, about 100 nm, about 120 nm, about 140 nm, about 150 nm, about 160 nm, about 180 nm, about 200 nm, about 220 nm, about 240 nm, about 260 nm, about 280 nm, about 300 nm, about 350 nm, about 400 nm, about 450 nm or about 500 nm. In one embodiment, the substrate includes a buried oxide layer. In a further embodiment, the buried oxide layer has a thickness of about 10 nm to about 500 nm. The buried oxide layer, in another embodiment, has a thickness of about 10 nm, about 20 nm, about 50 nm, about 60 nm, about 70 nm, about 80 nm, about 90 nm, about 100 nm, about 120 nm, about 140 nm, about 150 nm, about 160 nm, about 180 nm, about 200 nm, about 220 nm, about 240 nm, about 260 nm, about 280 nm, about 300 nm, about 350 nm, about 400 nm, about 450 nm or about 500 nm.

In a specific embodiment, the semiconductor layer has a thickness of about 190 nm. In a further embodiment, the semiconductor is silicon. In one embodiment, the substrate includes a silicon layer and a buried oxide layer, and the thickness of the buried oxide layer is about 150 nm. In one embodiment, the silicon is a p-type.

In one embodiment, the semiconductor material has a resistivity of about 5 Ω-cm to about 200 Ω-cm, inclusive. In another embodiment, the semiconductor material has a resistivity of at least about 5 Ω-cm, at least about 10 Ω-cm, at least about 20 Ω-cm, at least about 30 Ω-cm, at least about 40 Ω-cm, at least about 50 Ω-cm, at least about 60 Ω-cm, at least about 70 Ω-cm, at least about 80 Ω-cm, at least about 90 Ω-cm, at least about 100 Ω-cm, at least about 120 Ω-cm, at least about 140 Ω-cm, at least about 160 Ω-cm, at least about 180 Ω-cm or at least about 200 Ω-cm.

The semiconductor material, in one embodiment, is thinned down to an appropriate thickness, for example, about 50 nm, or about 75 nm, or about 100 nm, and a photoresist layer is coated on top of the semiconductor layer. In one embodiment, the photoresist comprises hydrogen silsesquioxane (HSQ). This photoresist layer is then defined into the multiwire structure of the present invention by a lithographical process, for example, a T-shape nanowire structure, or a multiwire structure where the wires are joined at an angle other than 90°. As provided above, in one embodiment, multiple sensing nanowires form nodes in between the first and second ends of the nanowire FET.

In one embodiment electron beam lithography is used to define the nanowires of the invention. In another embodiment, nanoimprint lithography is used to define the nanowires of the invention. In yet another embodiment, optical lithography is used to define the nanowires of the invention.

In one embodiment, the width of the nanowires ranges from about 10 nm to about 3000 nm. The dimensions of the wires can be varied by the electron beam lithography process. Each wire can have the same, about the same, or different dimensions (width, diameter, length, aspect ratio). In one embodiment, the width of at least one of the wires of the multiwire structure is about 10 nm, about 20 nm, about 30 nm, about 40 nm, about 50 nm, about 100 nm, about 150 nm, about 200 nm, about 250 nm, about 300 nm, about 500 nm, about 1 µm, about 2 µm or about 3 µm. In a further embodiment, the two wires of the multiwire structure (i.e., the nwFET of the present invention) have the same width, about the same width, or a different width. In yet another embodiment, the two wires of the multiwire structure (i.e., the nwFET of the present invention) have the same dimensions, about the same dimensions, or different dimensions.

In one embodiment, the length of the sensing nanowire and/or the nwFET is in the range of about 20 nm to about 30 µm. In one embodiment, the length of each of the sensing nanowire and the nwFET is independently about 50 nm, about 60 nm, about 70 nm, about 80 nm, about 90 nm, about 100 nm, about 110 nm, about 120 nm, about 150 nm and about 200 nm, about 500 nm, about 1 µm, about 2 µm, about 3 µm, about 4 µm, about 5 µm or about 10 µm, about 20 µm, or about 30 µM. In one embodiment, the lengths of the sensing nanowire and the nanowire FET are the same. In another embodiment, the lengths of the sensing nanowire and the nanowire FET are different.

In yet another embodiment, the two wires of the multiwire structure (i.e., the nwFET of the present invention) have the same aspect ratio, about the same aspect ratio, or a different aspect ratio (width:height). In one embodiment, the aspect ratio of each wire is selected from about 1:1, about 1:1.5, about 1:2, about 1:3, about 1:4, about 2:1, about 2:1.5, about 2:3, about 3:1, about 3.5:1, about 4:1.

Once the multiwire structure is defined, the source, drain, and base electrodes are formed. The electrodes slightly overlap the nanowire structures. The electrodes for use with the present invention are fabricated from a metal, metal alloy, metal oxide, mixed metal oxide (i.e., oxide coating over inert metal or carbon core) metal nitride or conducting polymer. In one embodiment, one or more of the electrodes is fabricated from aluminum, cesium carbonate, calcium dendrite, lithium fluoride, molybdenum(VI) oxide, lanthanum nickelate, lanthanum strontium cobalt ferrite, lanthanum strontium manganite, manganese cobalt oxide, nickel oxide, nickel(II) oxide, vanadium(III) oxide, vanadium(V) oxide, graphite, carbon, platinum, tin, palladium, nickel, gold, or silver, or a combination thereof. In one embodiment, the electrodes are formed by photoresist lift-off. In a further embodiment, the electrodes are formed by a photoresist lift-off of a sputtered platinum (Pt) on titanium (Ti) dual layer. The semiconductor regions unprotected by HSQ and metals are then removed by reactive ion etching followed by rapid thermal annealing, for example at 450° C. for 10 min. The annealing process, in one embodiment, is optional. However, the rapid thermal anneal is thought to help enhance device performance.

The devices described herein include either one or more Schottky contact/junctions (i.e., between a metal electrode and semiconductor) or one or more impurity doped contact/junctions or a combination thereof. Both types of junctions are known to those of ordinary skill in the art, and can therefore be fabricated according to the ordinary skill in the art. For example, in one embodiment, the impurity dopant is introduced into a semiconductor substrate by diffusion or ion implantation. Alternatively, the doped substrate is available commercially. In one embodiment, a doped substrate is used to fabricate the devices of the invention. In a further embodiment, the substrate is doped silicon. In even a further embodiment, the dopant is boron, phosphorus or gallium.

In one embodiment, the entire sensor is shielded from the ambient environment except on the sensing nanowire surface. Accordingly, the device surfaces, except for the sensing nanowire surface, are passivated to protect these portions of the device from interaction with the test solution during detection measurements. For example, in one embodiment, the devices are covered with a layer of silicon nitride, except above the sensing nanowire surface. The silicon nitride passivates the surfaces and therefore limits these surfaces from any interaction with the test solution during the detection measurements.

In one embodiment, the sensing nanowire is derivatized with a plurality of immobilized capture probes. The immobilized capture probes on each sensing nanowire can either be homogenous, i.e., specific for a single target (molecule, ion), or heterogeneous, i.e., specific for multiple targets (molecules, ions). In one embodiment, each of the plurality of capture probes comprises at least a free amino group, carboxyl group or hydroxyl group. In a further embodiment, an electrolyte solution (e.g., physiological solution) is introduced on the sensing nanowire of the device, and a change in pH results in a change in charge of the amino groups. The change in charge results in a fluctuation in the sensing nanowire current ($I_B$). This fluctuation is amplified and readout as the nanowire FET drain current ($I_D$). Accordingly, a change in drain current ($I_D$) is correlated with a change in pH of the solution.

Figure 15:
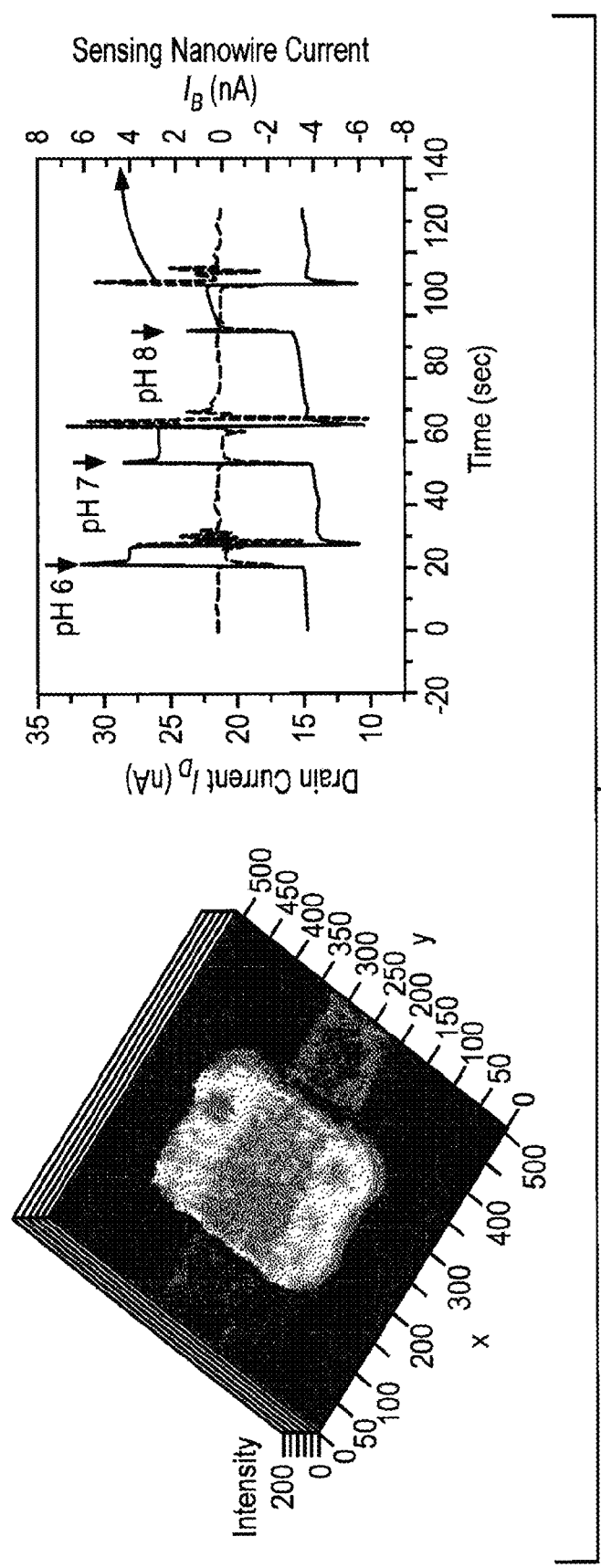
FIG. 15 (left) is a confocal microscope image of FITC bound to a 3 µm width silicon nwFET after APTES treatment.

In one embodiment, each immobilized capture probe forms a specific binding pair with a target molecule of interest. In one embodiment, the sensing nanowire is derivatized with immobilized capture probes through one or more linker molecules. For example, in one embodiment, 3-aminopropyltriethoxysilane (APTES) molecules are used as linkers. In another embodiment, APTES molecules are used to detect changes in pH (FIGS. 4, 6 and 15).

As provided above, the present invention provides a novel nwFET device which comprises, in one embodiment, two nanowires orthogonal to one another (FIG. 1). The device, in one embodiment, forms a T-channel structure by adding a sensing nanowire (also referred to as "sensing gate" or "SG") orthogonal to the nwFET channel (FIG. 1). In another embodiment, the device comprises multiple sensing nanowires, each with a base electrode associated with it (FIG. 2).

An applied sensing gate voltage ($V_{SG}$, also referred to herein as $V_B$) changes the potential of the entire channel and at the middle node as illustrated in the biasing schemes (FIG. 5). The T-nwFET operates as a regular nwFET sensor with a floating SG (FIG. 5, top). A more positive $V_{SG}$, splits the sensing gate current ($I_{SG}$) into source current ($I_S$) and drain current ($I_D$) yet it does not meaningfully modulate $I_D$ (FIG. 5, middle). Any current or voltage fluctuation in SG can thus effectively modulate the Schottky barrier height and/or width at the source electrode such that a modest amplification might be achieved. A more negative $V_{SG}$ (FIG. 5, bottom) would similarly allow the SG modulation over the Schottky barriers and achieve gain, yet the baseline current tends to be higher.

Mechanical, Biological and Chemical Sensing Assays

The device of the present invention, in one embodiment, is used to sense environmental stress. For example, in one embodiment, mechanical stress is detected by the device of the invention. In one embodiment, the device comprises a sensing nanowire having a first end and a second end and a nanowire FET having a first end and a second end, wherein the sensing nanowire and nanowire FET each comprise a semiconductor material, the first end of the sensing nanowire is connected to the nanowire FET to form a node. Additionally, the first end of the nanowire FET is connected to a source electrode, the second end of the nanowire FET is connected to a drain electrode, and the second end of the sensing nanowire is connected to a base electrode. In a further embodiment, the first end of the sensing nanowire is connected to the nanowire FET at an angle between about 10° and 170° (e.g., an angle between about 30° and 150°, or an angle between about 50° and 100°) to form a node.

In one embodiment, if the sensing nanowire undergoes some mechanical stress, for example, if the sensing nanowire is bent, the sensing nanowire current ($I_B$) changes from the baseline level. The sensing nanowire current ($I_B$) is intimately amplified and readout as the nanowire FET drain current ($I_D$). Accordingly, in one embodiment, the device of the present invention is used to detect mechanical stress.

In the methods provided herein, the nwFET devices described above are used to detect one or more biomolecules of interest, detect change of pH or change in ion concentration. In each assay, a test sample is introduced to the device so that it comes into contact with the sensing nanowire.

As used herein, the term "test sample" refers to a sample suspected of containing and/or being tested for one or more biomolecules, ions, analytes or chemicals of interest, i.e., one or more target molecules or target ions. In one embodiment, the target molecule is at least one bacterial antigen or at least one parasitic antigen. In one embodiment, influenza virus RNAs are used as target molecules for detection with the nwFET devices of the invention. In yet another embodiment, cations in an electrolyte solution are the target ions detected.

In one embodiment, the test sample is derived from a biological source, such as, a physiological fluid, including, but not limited to, whole blood, serum, plasma, interstitial fluid, saliva, ocular lens fluid, cerebral spinal fluid, sweat, urine, milk, ascites fluid, mucous, nasal fluid, sputum, synovial fluid, peritoneal fluid, vaginal fluid, menses, amniotic fluid, semen and so forth.

In another embodiment, the test sample is an electrolyte suspension or solution. In one embodiment, an electrolyte solution is formed upon the dissolution of some biological (e.g., DNA, polypeptides) or synthetic polymers (e.g., polystyrene sulfonate), termed polyelectrolytes, which contain charged functional groups.

Besides physiological fluids, other liquid samples may be used such as water, food products, and so forth, for example, for the performance of environmental or food production assays.

In another embodiment, gaseous material suspected of containing the analyte (target molecule or ion) may be used as the test sample. For example, the presence of one or more gases (toxic or otherwise) may be detected by the devices and methods of the invention. In a further embodiment, the gas is toxic and/or from an environmental source. In this embodiment, the one or more gases is the analyte (target). In one embodiment, the sensing nanowire current ($I_B$) is a function of the amount of gas in the sample. When a toxic gas is present, in one embodiment, it adsorbs to the surface of the sensing nanowire, which in turn alters the sensing nanowire current. Accordingly, in this embodiment, the sensing nanowire surface acts as the immobilization probe. As provided above, the sensing nanowire current ($I_B$) is intimately amplified and readout as the nanowire FET drain current ($I_D$). Accordingly, a change in $I_D$ is correlated with a change in toxic gas in the test sample. Gases for use as targets of the present invention include, but are not limited to: ammonia, arsenic, arsine, boron tribromide, boron trichloride, boron trifluoride, bromine, carbon monoxide, chlorine, diborane, cyanogens chloride, fluorine, formaldehyde, hydrogen azide, hydrogen sulfide, nitrogen dioxide, osmium tetroxide, phosgene, ozone, arsine, or a combination thereof.

A list of semiconductor oxide materials with targeted selectivity for specific gases is provided in Table 2, below. In one embodiment, one or more of these gases is detected in an environmental sample, or in an air sample (e.g., in an air quality monitoring assay).

TABLE 2

Non-limiting list of semiconductor oxides with targeted selectivity for specific gases.

| Oxide Type | Detectable Gas |
| --- | --- |
| $SNO_2$ | $H_2$, $CO$, $NO_2$, $H_2S$, $CH_4$ |
| $TiO_2$ | $H_2$, $C_2H_5OH$, $O_2$ |
| $Fe_2O_3$ | $CO$ |
| $Cr_{1.8}Ti_{0.2}O_3$ | $NH_3$ |
| $WO_3$ | $NO_2$, $NH_3$ |
| $In_2O_3$ | $O_3$, $NO_2$ |
| $LaFeO_3$ | $NO_2$, $NO_x$ |

In another embodiment, the test sample is an environmental sample, and the target is a gas present in the sample. For example, the target, in one embodiment, is carbon monoxide gas.

In another embodiment, the nwFET of the device is designed to detect radiation in a test sample. In one radiation sensing embodiment, the device comprises a sensing nanowire having a first end and a second end and a nanowire FET having a first end and a second end, wherein the first end of the sensing nanowire is connected to the nanowire FET at an angle between about 10° and 170° (e.g., an angle between about 30° and 150°, or an angle between about 50° and 100°), to form a node. Additionally, the first end of the nanowire FET is connected to a source electrode, the second end of the nanowire FET is connected to a drain electrode, and the second end of the sensing nanowire is connected to a base electrode. Upon introduction of an irradiated sample onto the sensing nanowire, the conductivity of the sensing nanowire is altered. This results in a change in the sensing nanowire current ($I_B$). The sensing nanowire current ($I_B$) is intimately amplified and readout as the nanowire FET drain current ($I_D$).

The test sample may be used directly as obtained from a biological or non-biological source. The test sample, in one embodiment, undergoes a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, amplification (e.g., PCR), etc. Moreover, it may also be beneficial to modify a solid test sample to form a liquid medium or to release the analyte.

The test sample, in one embodiment, is introduced onto the device through microfluidic channels, which are in fluid communication with the sensing nanowire of the device. In another embodiment, the test sample is introduced manually via a pipette or through robotics. In one embodiment, where a gaseous target is detected in a test sample, the sample is contained within a channel, so that the sample does not escape into the environment.

"Nucleic acid," as used herein, refers to both deoxyribonucleic acid (DNA) and ribonucleic acid (RNA). Additionally, the term "nucleic acid" encompasses artificial nucleic acid analogs such as peptide nucleic acid (PNA), morpholino-nucleic acid, locked nucleic acid (LNA), as well as glycol nucleic acid and threose nucleic acid.

In one embodiment, a PNA is a DNA analog in which a 2-aminoethyl-glycine linkage generally replaces the normal phosphodiester backbone. A methyl carbonyl linker connects natural as well unnatural nucleotide bases to this backbone at the amino nitrogens. PNAs are non-ionic (charge-less), achiral molecules and are not susceptible to hydrolytic (enzymatic) cleavage.

As used herein, the term "antibody" refers to an immunoglobulin molecule or immunologically active portion thereof, namely, an antigen-binding portion. Examples of immunologically active portions of immunoglobulin molecules include F(ab) and F(ab')$_2$ fragments which can be generated by treating an antibody with an enzyme, such as pepsin. Examples of antibodies that can be used in the present disclosure include, but are not limited to, polyclonal antibodies, monoclonal antibodies, chimeric antibodies, human antibodies, humanized antibodies, recombinant antibodies, single-chain Fvs ("scFv"), an affinity maturated antibody, single chain antibodies, single domain antibodies, F(ab) fragments, F(ab') fragments, disulfide-linked Fvs ("sdFv"), and antiidiotypic ("anti-Id") antibodies and functionally active epitope-binding fragments of any of the above.

The phrase "specific binding partner," as used herein, is a member of a specific binding pair. That is, two different molecules where one of the molecules, through chemical or physical means, specifically binds to the second molecule. In one embodiment, a "specific binding partner" is present on a device as an "immobilized capture probe." In addition to antigen and antibody specific binding pairs of common immunoassays, other specific binding pairs can include biotin and avidin, carbohydrates and lectins, nucleic acid duplexes, effector and receptor molecules, cofactors and enzymes, enzyme inhibitors and enzymes, and the like. Furthermore, specific binding pairs can include members that are analogs of the original specific binding members, for example, an analyte-analog or a mutated enzyme in one or more amino acid positions, or a mutated/altered (i.e., non-complementary) nucleotide sequence. Immunoreactive specific binding members include antigens, antigen fragments, antibodies and antibody fragments, both monoclonal and polyclonal and complexes thereof, including those formed by recombinant DNA molecules.

A specific binding partner, once immobilized on the test device, is referred to as an "immobilized specific binding partner" or an "immobilized capture probe". Immobilization, in one embodiment, is through a linker molecule such as APTES.

In nucleic acid embodiments, a specific binding pair can be "perfect" or "non-perfect". A perfect specific binding pair comprises two nucleotide sequences that are complementary to each other. In one non-perfect specific binding pair embodiment, the two nucleic acid sequences are non-complementary in at least one position, or at least two positions, or at least three positions, or at least four positions, or at least five positions. For example, there may be a mismatch between the two sequences, or a deletion in one of the sequences. Nucleic acid mutations, in one embodiment, are caused by tautomerism, depurination, deamination, strand mispairing, or by a mutagen (e.g., ultraviolet light). The present invention, in one embodiment, distinguishes between perfect and non-perfect binding pairs by the difference in drain current ($I_D$).

In one embodiment, the present invention is used as a point-of-care diagnostic device. The nanoelectronic biosensor includes a regenerable detection scheme and can be tailored to detect a multitude of analytes (e.g., peptide nucleic acids (PNA), nucleic acids, antigens, antibodies, enzymes, hormones, etc.). In one embodiment, the devices provided herein are used to detect specific nucleic acid molecules (e.g., viral RNA or DNA). Viral RNA from influenza, hepatitis, HIV and HSV, in one embodiment, are detected by the devices and methods provided herein. Capture probes specific to the nucleic acid (complementary nucleic acid) are immobilized on the nanowire FET device, at the sensing nanowire surface, and a test sample is introduced onto the device.

In one embodiment, bioreceptor capture probes (e.g., PNA) are immobilized onto the sensing nanowire surface and the test sample is introduced from above. Target molecules (e.g. viral RNA), if present in the test sample, form specific binding pairs with the immobilized capture probes. The electric field emanated from the charges on the bound molecules is then coupled to modulate/alter the sensing nanowire conductance. The resultant signal change in drain current ($I_D$) is intimately amplified with minimal parasitics by the built-in nanowire transistor to achieve a sufficient sensitivity, and is electronically read out.

Multiplex detection is also readily accomplished with multiple T-nwFETs where each individual sensing nanowire includes a different immobilized capture probe, specific for a unique target or disease. In another embodiment, a single device includes different capture probes on a single sensing nanowire, to provide for multiplex detection.

In order to control for non-specific binding and false positives, in one embodiment, a two-step specific binding approach is carried out. For example, in one embodiment, a test sample is introduced onto the device, and is allowed to interact with the sensing nanowire. If the test solution includes the target molecule(s), it will bind the immobilized capture probe present on the sensing nanowire, to form a specific binding pair complex. Next, the test solution is removed and an additional binding reagent, which binds the specific binding pair complex, is introduced to provide a second level of specificity. These methods require additional agents and mixing steps, and can be implemented by those of ordinary skill in the art.

In one embodiment, the target molecule is first specifically amplified prior to introducing it onto the test device. For example, a polymerase chain reaction, in one embodiment, is carried out on the nucleic acids in the test sample prior to introducing the test sample onto the device. In another embodiment, the detection signal (e.g. electronic charge) on each bound target molecule is amplified prior to determining the amount and/or identity of bound target molecule (e.g., nucleic acid or protein analyte).

If the test sample includes one or more target molecules, it will hybridize to the device through one or more immobilized capture probes (i.e., immobilized specific binding partners) present on the sensing nanowire. Upon hybridizing, the conductance of the device is altered. An altered conductance signifies that a binding event has occurred. Degree of the change also indicates how many binding events took place.

In one embodiment, the nwFET device of the invention is used to detect nucleic acid target molecules, for example to detect viral nucleic acids in a diagnostic assay. In this embodiment, the sensing nanowire surface is covalently functionalized with nucleic acid molecules complementary to one or more target nucleic acids, or PNA immobilized capture probes complementary to the one or more target nucleic acids. Next, the test sample is introduced, which may include target nucleic acid, e.g., viral RNA target molecules (i.e., at $t_1$ in FIG. 18). In one embodiment, upon binding of the target to its complement and forming a specific binding pair, the T-nwFET current, increases from $I_{blank}$ to $I_{detected}$.

In one embodiment, a target molecule in the test sample is not fully complementary to its specific binding partner, and therefore, a non-perfect binding pair is formed. In this embodiment, there is at least one difference between the specific binding partners' nucleic acid sequences. In one embodiment, the non-perfect pair comprises two nucleic acid molecules, and one nucleic acid sequence has a deletion, mismatch compared to the second nucleic acid sequence.

In another embodiment, the device and methods provided herein allow for the detection of variations in a protein's amino acid sequence. In one embodiment, the immobilized capture probe binds a protein as well as a mutated version of the protein. For example, a first protein, in one embodiment, has an amino acid mutation compared to the second protein. In this embodiment, the electrical properties of the device differ depending on which binding event occurs (i.e., whether the mutant or non-mutant binds).

Figure 18:
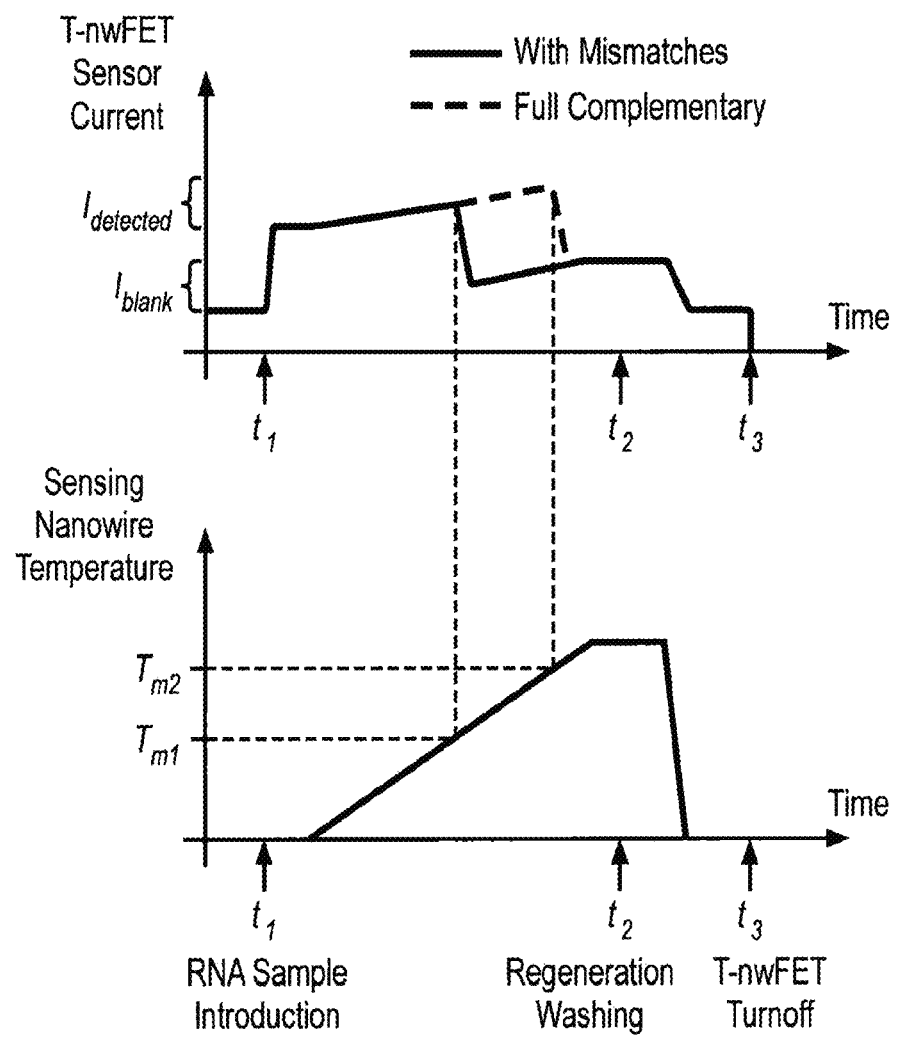
FIG. 18 are two graphs showing theoretical sensor current vs. time (top) and nanowire temperature vs. time at various stages of sample processing.

In one nucleic acid embodiment, there exists a small number of non-specific bindings or hybridizations with base-pair mismatches with either one or more non-target nucleic acid molecules (noise), or one or more target nucleic acid molecules (solid curve in FIG. 18 (top)). In this embodiment, the immobilized capture probe (specific binding partner) is designed to be non-complementary, so that it captures the one or more target nucleic acid molecules which include the non-complementary and/or mutated sequence(s).

The sequences of two different captured nucleic acids (i.e., the two target molecules, each with a different sequence), in one embodiment, are distinguished by the melting temperature of the various nucleic acid duplexes (i.e., dashed trace in FIG. 18, top). After reaching the steady-state temperature, in one embodiment, the sensing nanowire temperature is continuously and controllably ramped up (FIG. 18, bottom). This in turn increases the current $I_{detected}$ (or $I_{blank}$ if no target is bound to its complement/specific binding pair member).

Figure 19:
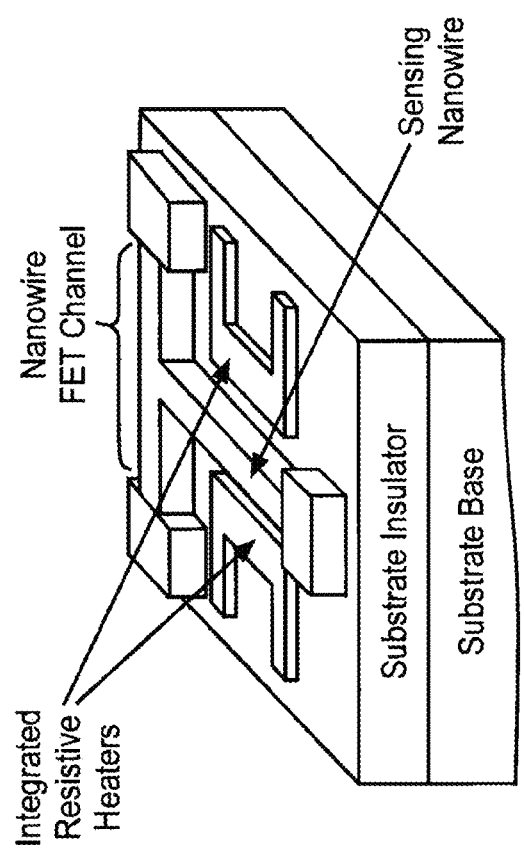
FIG. 19 is a T-nwFET structure with neighboring integrated resistive heaters.

The required highly localized heating required for melt analysis, in one embodiment, is accomplished using integrated resistive heaters in close proximity to the sensing nanowire (FIG. 19). In another embodiment, the device is placed on a heating block to carry out melt analysis. The resistive heaters, in one embodiment are constructed from one or more conventional integrated circuit manufacturing materials. For example, titanium, platinum, nickel, or silicon, or a combination thereof, can be used to manufacture the heaters.

The integrated resistive heater structure and performance, in one embodiment, are designed with the use of finite element simulations. In one embodiment, the temperature of the nanowire device is calibrated against the heaters' input current by measuring the temperature-dependent nwFET leakage current.

Nucleic acid duplexes (e.g., RNA-PNA, RNA-RNA, DNA-DNA, DNA-RNA and DNA-PNA duplexes) with one or more base-pair mismatches exhibit a lower melting temperature ($T_{m1}$) than that of their fully complementary counterpart ($T_{m2}$). Similarly, proteins with different amino acid sequences exhibit different melting temperatures, when binding to a different protein. For example, antibodies with different amino acid sequences, in one embodiment, bind the same antigen with different disassociation constants, and therefore, exhibit different melting temperatures.

In one embodiment where a non-perfect binding pair is formed, during melt analysis, the respective T-nwFET $I_{detected}$ reduces to an intermediate level before returning to near the $I_{blank}$ level (solid curve in FIG. 18) before the complementary duplex does (dashed trace in FIG. 18). The reduction of I at $T_m$ represents the binding and removal of the specific target sequence from its complement (i.e., the target molecule is no longer present in a specific binding pair). This allows for regeneration of the device as well as detection of variations in nucleotide sequences of target molecules.

Although the devices provided herein may be regenerated to allow for multiple uses, the devices may need to be replaced under certain circumstances. For example, a device of the invention may not be reusable if the $I_{blank}$ level becomes too close to the $I_{defected}$ over time due to cumulative fouling of molecules/particles, or if sensors, heaters, or immobilized capture probes are naturally worn off after repeated use (e.g., after 10-100 times).

In one embodiment, a counter ion screened electric field, which relies strongly on the background ionic strength and perfect vs. non-perfect (e.g., mismatched nucleic acid strands) binding pairs, is applied to the nwFET device, to allow for dehybridization of the target nucleic or target protein from the immobilized capture probe, i.e., to separate the specific binding pair members. In one embodiment, regeneration of the whole detection scheme is carried out.

In one embodiment, to ensure complete melting, the sensing nanowire temperature is continuously increased to be slightly above $T_{m2}$ (i.e., the $T_m$ of the full complement), and then stabilized (FIG. 18, bottom). In one embodiment, after temperature stabilization, a regeneration washing step with detergent is applied to remove all melted nucleic acids and the remaining test sample solution (i.e., at $t_2$ in FIG. 18). The sensing nanowire temperature is then ramped down. For example, if a heating block is used, the heating block is turned off. Similarly, if integrated resistive heaters are used, these are switched off to ramp down the sensing nanowire temperature. The decrease in temperature and removal of specific binding pairs return the current to $I_{blank}$ level. During this process, the sensor current is monitored to reset to $I_{blank}$ (FIG. 18, top). Finally, the T-nwFET is turned off (i.e., at $t_3$ in FIG. 18) to minimize energy consumption and to ready the device for reusage in a subsequent next detection cycle.

As provided above, in one embodiment, the multiwire nanowire FET devices provided herein allow for the formation of perfect and non-perfect binding pairs. In order to distinguish between these type of binding pairs, for example, in order to distinguish between the binding of a complementary nucleic acid to an immobilized capture probe (i.e., a perfect binding pair) and the binding of a non-complementary nucleic acid sequence to the same immobilized capture probe (i.e., a non-perfect binding pair), in one embodiment, certain thermodynamic factors are considered. In another embodiment, these same factors are taken into consideration when distinguishing between the binding of two proteins with different sequences to the same immobilized capture probe (e.g., where one protein has an amino acid mutation compared to the other).

For example, the following factors are useful in determining whether a melt analysis may be carried out:

A. Sufficient difference between and $T_{m1}$, $T_{m2}$ (FIG. 18).
B. Thermal stability of the immobilized (e.g., covalently immobilized) probe during the heating cycle.
C. No subsequent annealing or elongation of the nucleic acid melts during the cooling from $t_2$ to $t_3$.

Regarding factor A, there exist data on the thermal stabilities of nucleic acid duplexes that are either fully complementary or include base-pair mismatches. Compared to the fully complementary duplex, duplexes with a 1 base-pair mismatch may have a $T_m$ that is 8-10° C. lower. Additionally, it has been shown previously that although the RNA-PNA duplexes have on average a 4° C. higher $T_m$ than the DNA-PNA duplexes, both duplex types exhibit about the same quantitative $T_m$ variation with mismatches. Consequently, a difference in $T_m$ is available to distinguish between a perfect complement binding and a non-perfect complement binding to the same specific binding partner. These considerations are also applicable when dealing with proteins of varying sequence, captured by the same immobilized capture probe.

In one embodiment, a binding specific when it has over 15 out of 17 base-pairs matching perfectly. Such a match is sufficient to distinguish specific pathogens and host genomes. In one embodiment, the nwFET drain current differs upon the binding of an oligonucleotide to the sensing nanowire having single base mismatch, when compared to an oligonucleotide having a two-base mismatch, or an oligonucleotide which is a perfect complement to the immobilized capture probe.

$T_m$ values of nucleic acid duplexes, in one embodiment, are initially estimated using the nearest-neighbor thermodynamic models and subsequently verified during experimentation and device calibration.

Factors B and C are also fulfilled by the present invention. The covalent immobilization of specific binding partners (i.e., immobilized capture probes) onto the sensing nanowire should be stable, e.g., dissociation of the immobilized capture probe occurs at temperatures greater than 200° C., while the $T_m$ values for all the specific binding pairs of interest are <100° C. Additionally, elongation does not occur because the reagents necessary for this process are not present in the test sample, even though the sensing nanowire might reach the necessary elongation temperature during cooling.

Figure 17:
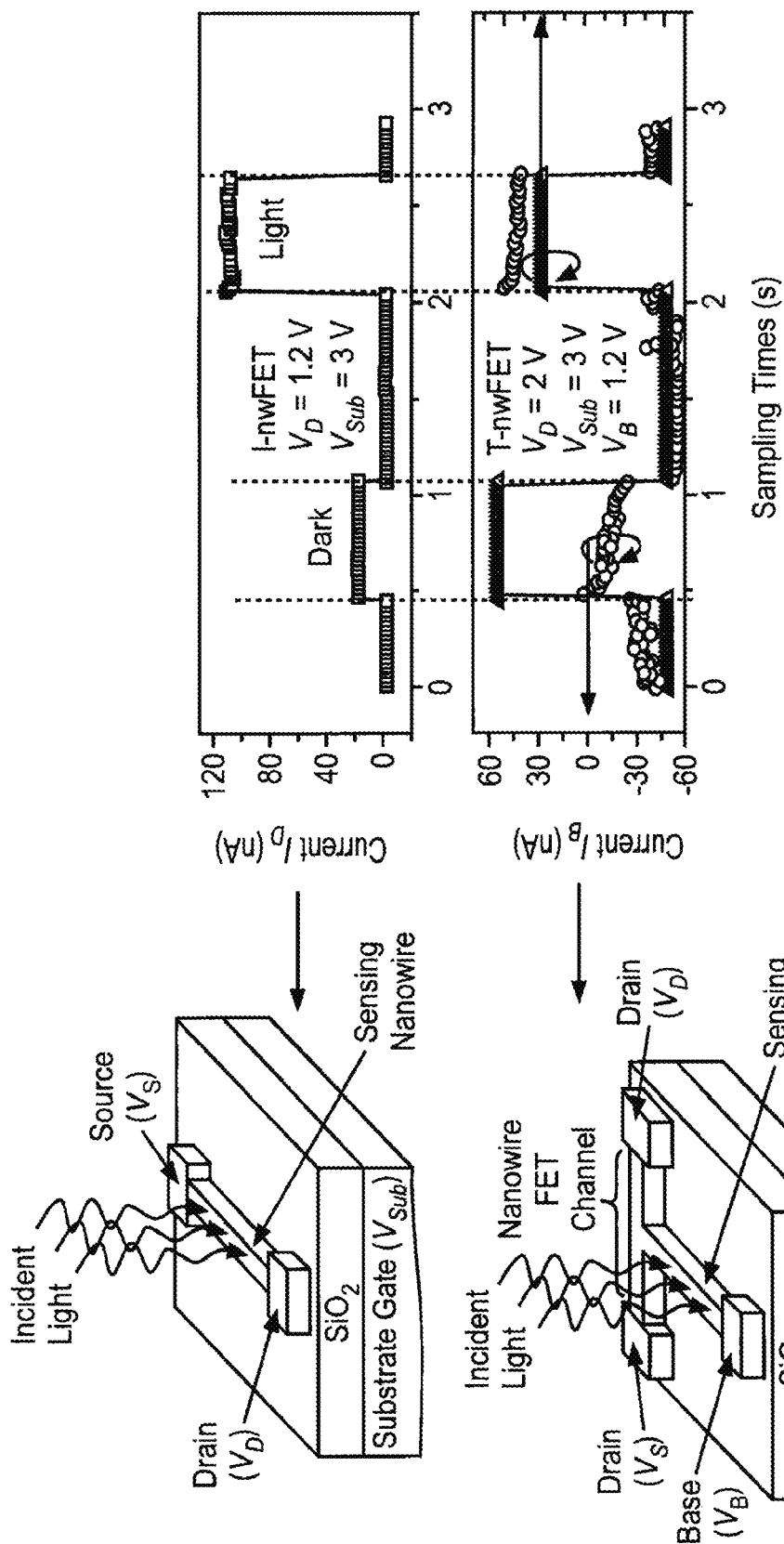
FIG. 17 provides two graphs showing $I_D$ (nanowire FET drain current) and $I_B$ (sensing nanowire current) as a function of sampling time, during real-time sensing of incident microscope light by the bulk sensing nanowire in (top) the generic Schottky single wire nwFET $I_D$ and (bottom) the Schottky T-nwFET $I_B$. The sensing nanowires in each device are 10 µm long and 100 nm wide.

In addition to the above theoretical considerations, control over the sensing nanowire temperature should also be considered. Since the nanowire ambient is warmed by local heaters (FIG. 17) or a heating block, via joule heating, the nanowire temperature can be pre-calibrated against the heaters' input current in the same sample solution environment prior to the actual target molecule(s) detection(s). It should be noted that contrary to applications that require high temperature precision (e.g., DNA melting analysis for mutation scanning and genotyping), the requirements here are more relaxed (on the order of few ° C.) because of the sufficiently large difference in $T_m$ of the perfect duplex and non-perfect duplex.

The procedural duration of the detection scheme, in one embodiment, depends on both the nanowire temperature ramp and the specific binding pair (e.g., nucleic acid duplex, or protein-protein complex) dissociation rate. The former is determined by the heating rate of the heaters (e.g., locally integrated heaters) and sample solution volume. The latter is governed by the specific binding pair melting kinetics. The whole thermal cycle, including the regeneration washing step, in one embodiment, lasts approximately 10 minutes (see FIG. 18).

In one aspect, a method for detecting the change in pH in a sample is provided. In one embodiment, the method comprises measuring the baseline drain current ($I_D$) associated with a nwFET device comprising a sensing nanowire having a first end and a second end and a nanowire FET having a first end and a second end, wherein the first end of the sensing nanowire is connected to the nanowire FET at an angle between about 10° and 170° (e.g., an angle between about 30° and 150°, or an angle between about 50° and 100°), to form a node. The first end of the nanowire FET is connected to a source electrode, the second end of the nanowire FET is connected to a drain electrode, and the second end of the sensing nanowire is connected to a base electrode. The sensing nanowire is derivatized with free amino groups. The method further comprises introducing a test sample onto the sensing nanowire, and measuring the change in $I_D$ after introduction of the sample, wherein a change in $I_D$ is associated with a change in pH of the test sample.

In yet another aspect, a method for detecting the presence or absence of a target molecule in a sample is provided. In one embodiment, the method comprises measuring the baseline drain current ($I_D$) associated with a nwFET device comprising a sensing nanowire having a first end and a second end and a nanowire FET having a first end and a second end, wherein the first end of the sensing nanowire is connected to the nanowire FET at an angle between about 10° and 170° (e.g., an angle between about 30° and 150°, or an angle between about 50° and 100°), to form a node. The first end of the nanowire FET is connected to a source electrode, the second end of the nanowire FET is connected to a drain electrode, and the second end of the sensing nanowire is connected to a base electrode. The sensing nanowire is derivatized with a plurality of immobilized capture probes that are specific for a target(s) (analyte) of interest. The method further comprises introducing a test sample onto the sensing nanowire, and measuring the change in $I_D$ after introduction of the sample, wherein a change in $I_D$ is associated with the target (analyte) of interest binding the device.

Test Strips

In one embodiment, the T-nwFET of the invention is integrated into a medical device in the form of a test strip, inside a battery-operated or self-powered hand-held digital meter (similar to a glucose meter). In one embodiment, a small drop of test sample (e.g., blood), is placed on the test strip comprising the multiwire structure, and the electrical properties before and after the sample is applied are compared, to determine whether the molecule of interest was present in the test sample. For example, in one embodiment, the drain current of the device ($I_D$) is altered upon introduction of the sample onto the test strip.

EXAMPLES

The present invention is further illustrated by reference to the following Examples. However, it should be noted that these Examples, like the embodiments described above, are illustrative and are not to be construed as restricting the scope of the invention in any way.

Unless otherwise indicated, the materials used in the following examples were prepared according to the following methods and procedures.

Device Design and Fabrication

Figure 9:
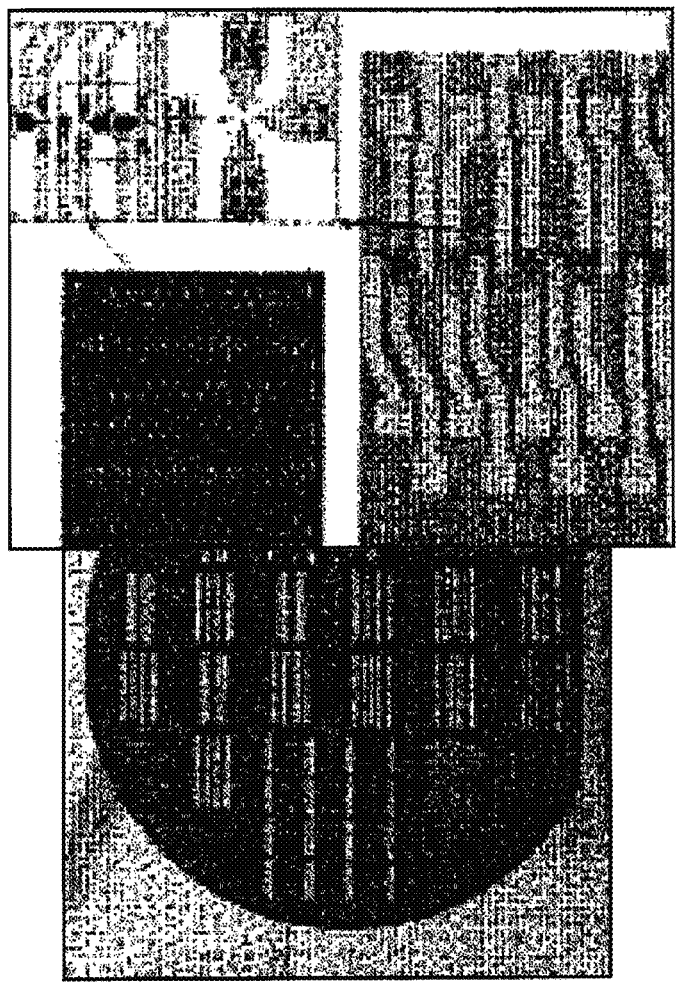
FIG. 9 shows the wafer and die photographs of T-nwFETs fabricated together with images of the design layout.

Si T-nwFETs were designed and fabricated on silicon-on-insulator (SOI) substrate using CMOS compatible process (FIG. 9). P-type SIMOX (Separation by IMplanted OXygen) SOI wafers with a resistivity of 10-20 Ohm-cm were used as a starting material. Each wafer a 190 nm thick SOI layer on top of 150 nm thick buried oxide (BOX).

The SOL layer was first thinned down to 50 nm followed by the T-channel mesa patterning with e-beam lithography. Source, drain, and SG (base) electrodes were then formed by Pt/Ti liftoff using conventional lithography. The exposed Si region was removed by reactive ion etching followed by a rapid thermal anneal at 450° C. for 10 min. to sinter the metal-Si contacts.

Schottky single wire FET sensors of the same width were fabricated for control purposes.

Figure 10:
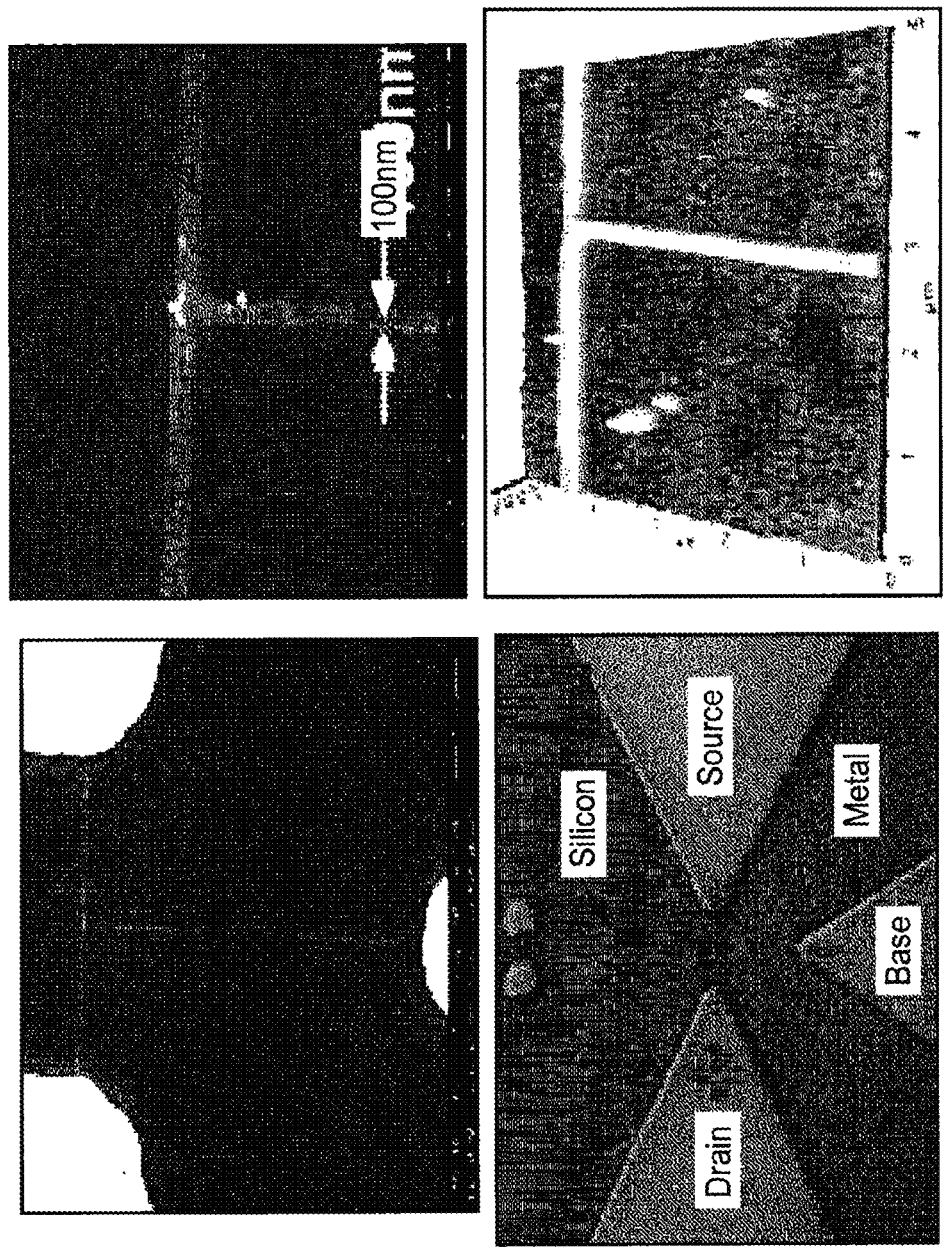
FIG. 10 shows Atomic Force Microscopy (AFM) (bottom) and scanning electron microscopy (SEM) images (top) of a 100 nm wide T-nwFET.

AFM (FIG. 10, top right) and SEM images (FIG. 10, bottom) of a finished 100 nm wide T-nwFET are shown in FIG. 10. After measuring the electrical characteristics of fabricated Si T-nwFETs (and co-fabricated single wire FETs), all devices were covered with a 300 nm of LPCVD silicon nitride (except above the sensing nanowire regions) to passivate them from any interaction with the electrolyte during pH sensing or analyte (target molecule) measurement.

Example 1

Si T-nwFET Device Characterization

DC characteristics of the nwFET channel were measured. The device included a 10 μm long and 100 nm wide sensing nanowire and nanowire FET channel.

Figure 11:
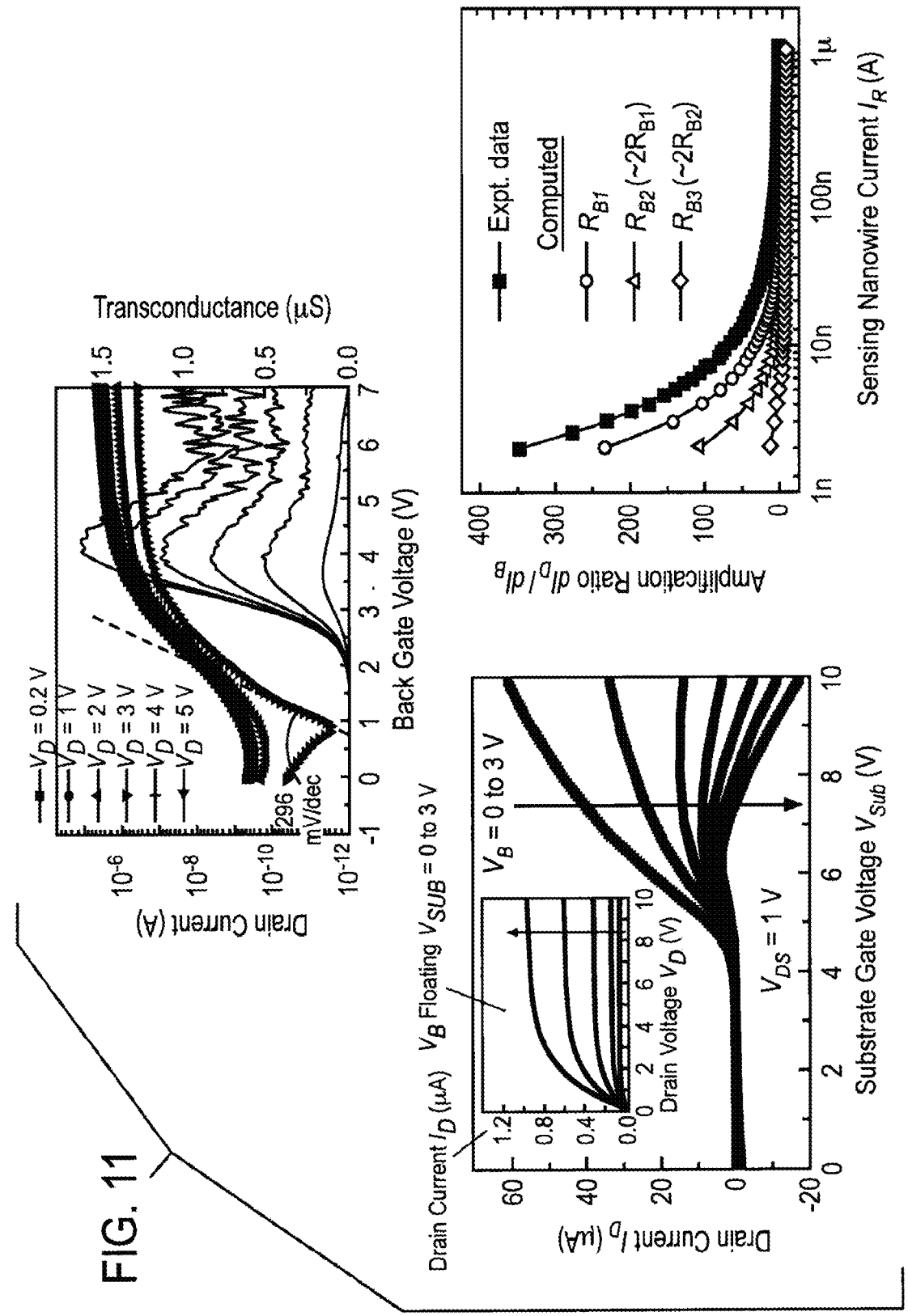
FIG. 11 are graphs showing the basic DC characteristics of a Si T-nwFET of the invention.

Results showed an inverse sub-threshold slope S ~294 mV/decade at 0.2 V drain voltage (FIG. 11). Additionally, the gate voltage-drain current transfer characteristics were shifted to the left with an increased drain voltage (FIG. 11, top). Without wishing to be bound by theory, the shift was thought to be due to the reduction of the Schottky barrier by the drain potential similar to the dram-induced barrier lowering (DIBL) effect in a MOSFET. Thus, a higher minimum drain current in the off-state was obtained.

When the base electrode (i.e., the sensing nanowire) was floated, the output characteristics across the source and drain electrodes with a varying substrate gate voltage, $V_{Sub}$ (inset in FIG. 11, bottom left), resembled those of a conventional Schottky nwFET. These data verified the baseline integrity of the fabrication process.

With a nonfloating and varying $V_B$, the T-nwFET transfer characteristics, i.e., $I_D$-$V_{sub}$, were also extracted (FIG. 11, bottom left). When $V_B$ is small (e.g., <0.5 V), the T-nwFET behaves as a regular nwFET, and $I_D$ flows into the channel from the drain. When $V_B$ is increased, $I_n$, will also be raised so as to reduce the voltage difference ($V_D$-$V_n$). According to Equation (2), above, $I_D$ would thus decrease to zero and finally becomes negative.

Moreover, the anticipated current amplification in the novel T-nwFET was confirmed. The $I_D$-$I_B$ characteristics were first obtained by injecting a varying amount of $I_B$ from the measurement system followed by taking their derivatives (FIG. 11, bottom right). The resultant amplification ratio versus $I_B$ behavior was adequately modeled by computing the $dI_D/dI_B$ ratio, as discussed above (FIG. 11, bottom right).

More importantly, these amplification ratios can be adjusted by the resistance values as guided by the above numerical approach.

Figure 12:
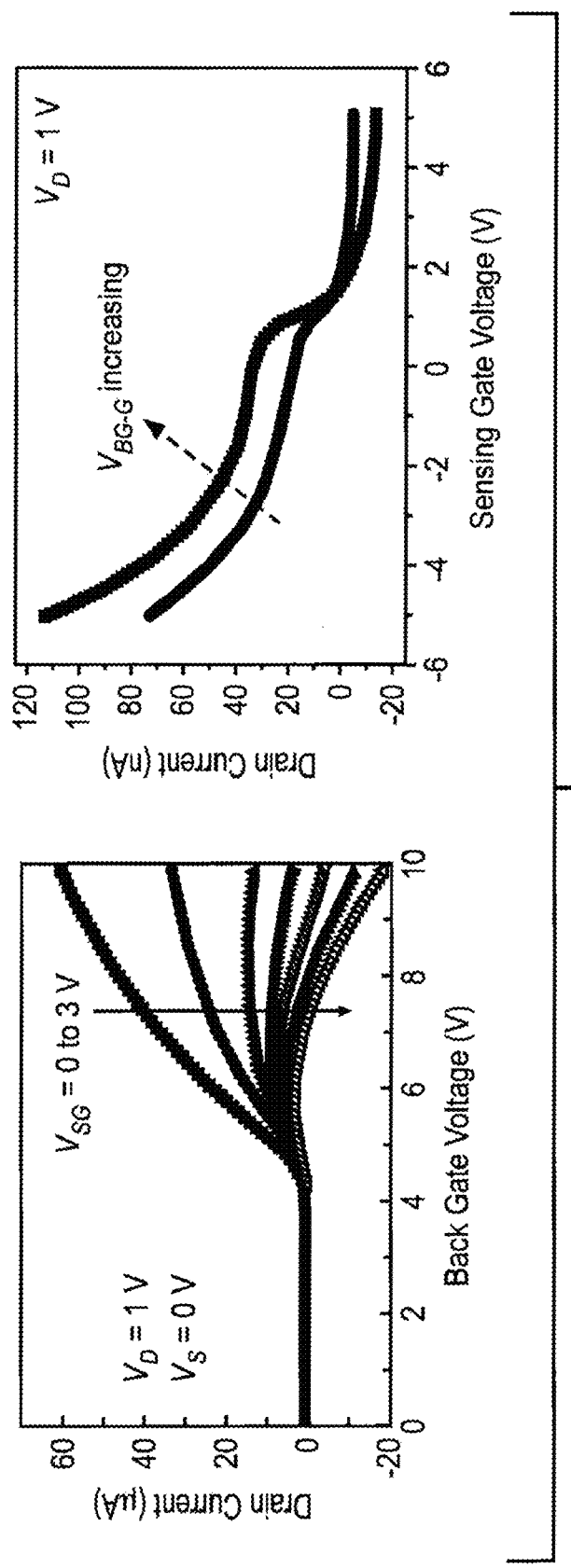
FIG. 12, left, is a graph showing the change in drain current as a function of back gate voltage (i.e., back gate biasing).

A large positive $V_{SG}$ turned $I_D$ to negative (FIG. 12, left). The absolute value of $I_D$ was also smaller than that under a negative $V_{SG}$ (FIG. 12, right) as explained in FIG. 5.

Figure 13:
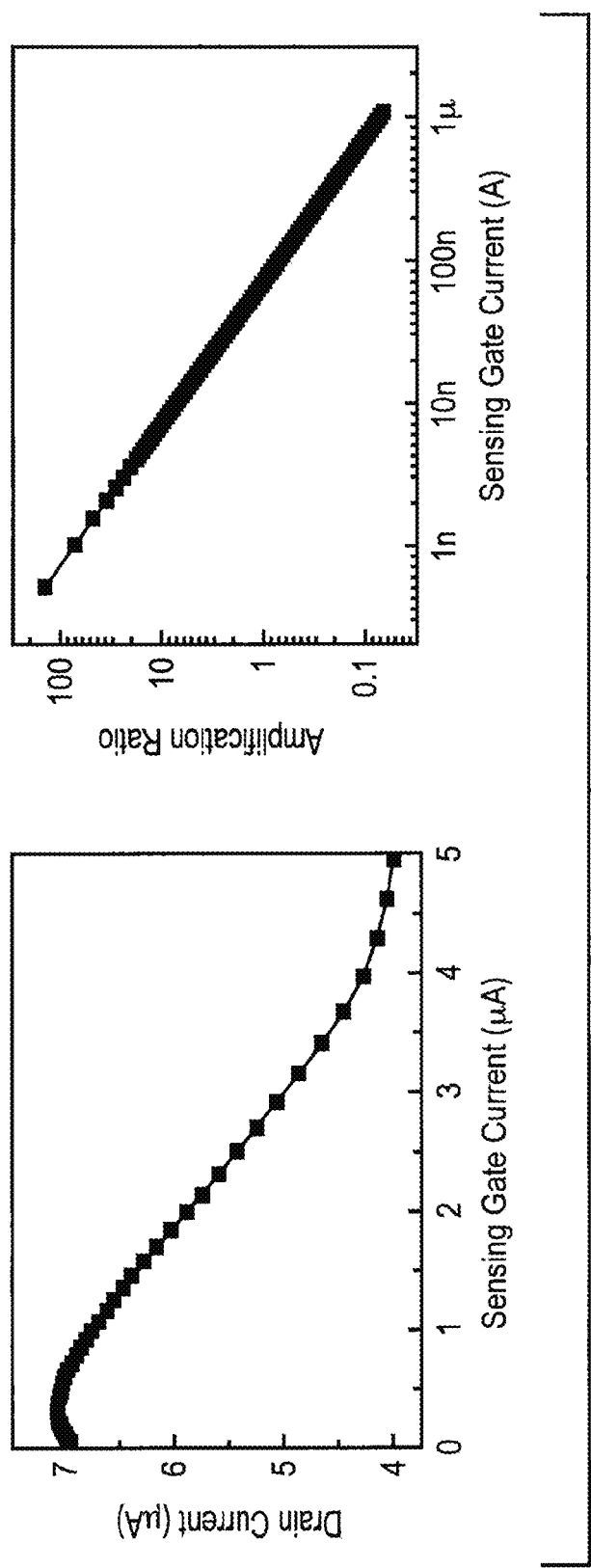
FIG. 13, left, is a graph showing the measured change in drain current as a function of sensing gate current.

The anticipated current amplifications were confirmed by injecting $I_{SG}$ from the measurement system (FIG. 13, left). A DC amplification factor ($I_D/I_{SG}$) as large as 100 was accomplished (FIG. 13, right).

Example 2 pH Sensing Measurements with the Si T-nwFET Compared to a Conventional Si nwFET

Figure 14:
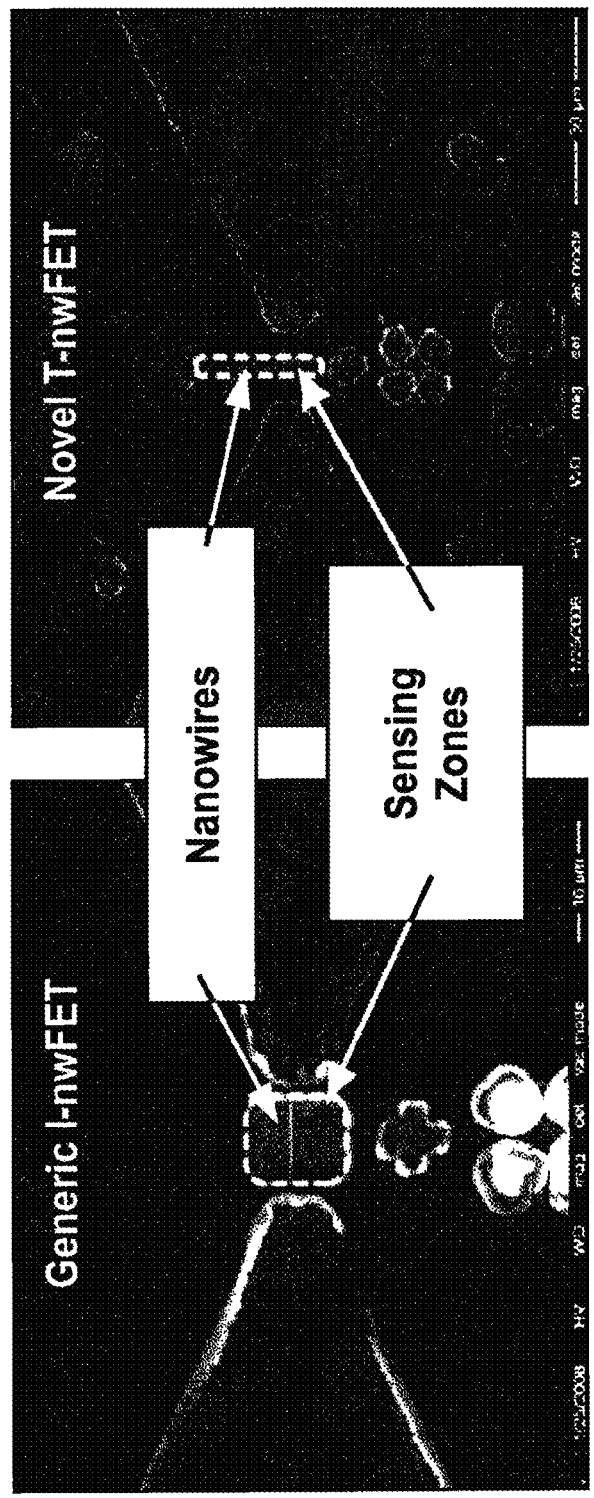
FIG. 14 shows SEM images of nitride passivated nwFET for pH and PSA sensing. Left: single wire Si nwFET sensor. Right: Si T-nwFET sensor of the present invention (multiwire).

T-channel devices used in these studies were fabricated as described above. SEM images of the conventional nanowire and T-channel nanowire device are provided in FIG. 14.

In order to detect hydrogen ion concentration (or pH), the sensing Si nanowire surface was first functionalized with 3-aminopropyltriethoxysilane (APTES) molecules to form exposed amino groups (—$NH_2$) (FIG. 6). These groups act as receptors of hydrogen ions that undergo the protonation or deprotonation reactions. An increase in the ambient pH increases the negative charge density on the nanowire surface and thus changes the nanowire conductance.

During the actual sensing operation, the $V_{SG}$ bias was fixed such that an ambient pH variation on the SG surface directly changed its conductance and thus $I_{SG}$. The potential at the middle node was then modulated. This in turn resulted in the Schottky barrier height and/or width modulation, which regulated the carriers that flowed across. Amplification was thus achieved like in a transistor. These proposed band profiles have been confirmed with device simulations (FIG. 7). It should be noted that in order to achieve a high gain, both the sensing nanowire and channel middle node dimension should have nanoscale dimensions, i.e., the dimensions provided for the devices described herein.

Comparison with Conventional Si nwFET

The sensing behavior of Si T-nwFET was compared with the co-fabricated Si nwFET. Images of the two devices are provided in FIG. 14. The sensing nanowire (sensing gate) in the T-nwFET was not passivated with a silicon nitride layer, while the rest of the device was passivated. The single wire device was not passivated with silicon nitride. Both devices were dipped in ethanol with 2% APTES for 1 hr. and then rinsed several times in ethanol. The devices were then baked in oven at 100° C. for 10 min. The stable APTES surface functionalization was examined with the fluorescein isothiocyanate (FITC) binding (FIG. 15, left).

A sample real-time measurement of changing ambient pH by the T-nwFET is displayed in FIG. 15, right. The drain current (i.e., output signal) decreased with an increasing pH value. Without wishing to be bound by theory, it is thought that the relationship between output signal and increasing pH value depends on the $V_{SG}$ and $V_{BG\text{-}S}$ biasing combination.

Figure 16:
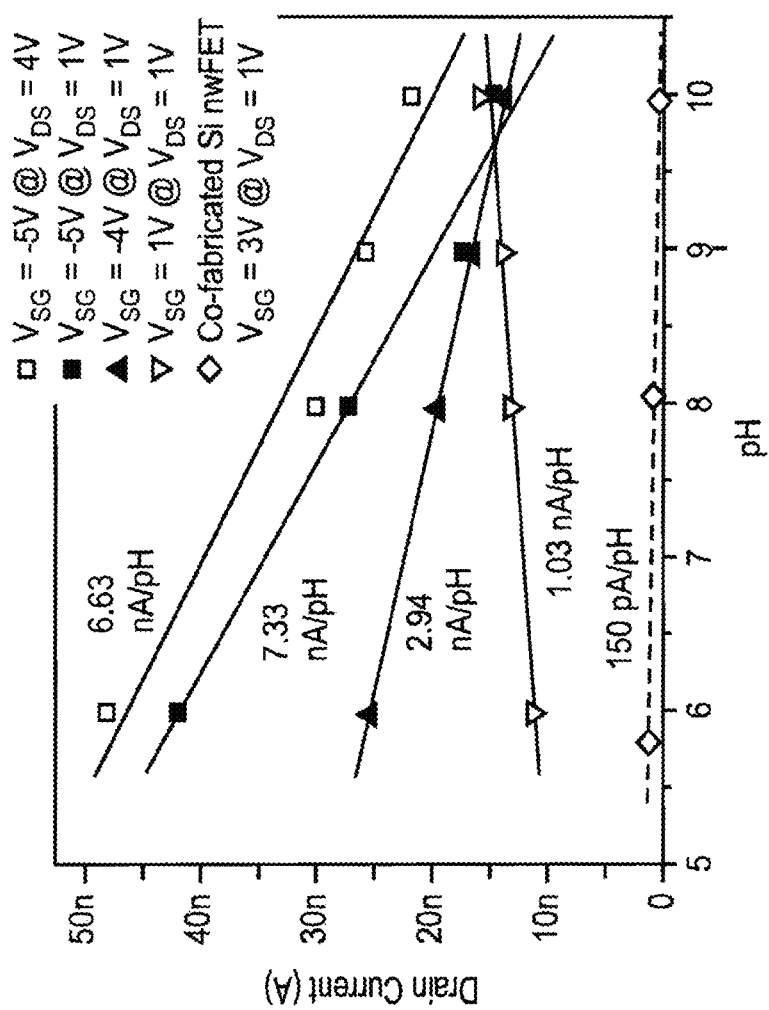
FIG. 16 is a graph showing the results of pH sensing with the T-nwFET of the present invention compared to a conventionally fabricated Si nwFET. Results are shown as drain current (output signal) as a function of pH. Sensing gate and back gate biasing was altered.

For objective comparisons between the novel T-nwFET and co-fabricated nwFET, the output signals were extracted and plotted against the pH value for various $V_{SG}$, $V_{DS}$, and/or $V_{BG}$ biasing combinations (FIG. 16). Each solid line joined the $I_D$ data from the T-nwFET with the same biasing combination. The dashed line alternatively merged the $I_D$ values from the nwFET. Both devices were capable to track the ambient pH change between 6 and 10.

Compared with the conventional nwFET, a 7 to 49 times higher sensitivity was obtained in the novel T-nwFET. The sensitivity values were extracted from the slopes in FIG. 16. It was observed that $V_{SG}$ is a more sensitive parameter than $V_D$ from the perspective of detection sensitivity.

Example 3

Bulk Sensing Performance of the T-nwFET

The bulk sensing performance of the novel T-nwFET was examined against that of the cofabricated Schottky I-nwFET (i.e., single channel nanowire) in this study. The detection of the probe station microscope light was chosen for the study with the assumption that the light intensity would stay constant throughout. While the entire I-nwFET was unshielded, only the sensing nanowire in T-nwFET was exposed by shadowing the source and drain nanowire channels and Schottky contacts with a Teflon mold. The light was turned off initially for about 1.5 s and then turned on, and biasing voltages were applied to the devices under test for 0.6 s duration in each lighting condition.

Real-time measurements of $I_D$ (for I-nwFET), and $I_B$ and $I_D$ (for T-nwFET) were taken as shown in FIG. 15. The I-nwFET $I_D$ level with light was higher than in dark because the incident light reduces the nanowire resistance at fixed $V_D$ and $V_S$. The T-nwFET $I_B$ and $I_D$ levels exhibited, however, an opposite trend. This can be understood that although $R_B$ does reduce with illumination, the potential difference ($V_B$-$V_n$) lowers even further that in turn induces a ($V_D$-$V_n$) drop. Since all terminal voltages are fixed throughout, both $I_B$ and $I_D$ should be decreased according to (1) and (2).

For a fair comparison, their respective biasing voltages for I- and T-nwFETs were chosen such that the amount of $|\Delta I_D|$ (90 nA) in I-nwFET due to illumination is similar to the $|\Delta I_B|$ (47-75 nA) in T-nwFET. In doing so, the resultant enhanced $|\Delta I_D|$ (2.3 µA) in T-nwFET can be elucidated by intrinsic amplification (of 31-49) since only the sensing nanowire was illuminated. These extracted current values and corresponding voltage biasing are listed in Table 3 below (cases A and C).

TABLE 3

Photodetection performance of control I-nwFET and T-nwFET under different biasing configurations

| | Case | | | |
|---|---|---|---|---|
| | A | B | C | D |
| Device (setup) | I-nwFET | I-nwFET | T-nwFET (S/D shadowed) | T-nwFET (all exposed) |
| $V_D$ | 1.2 V | 2.0 V | 2.0 V | 2.0 V |
| $V_{SUB}$ | 3.0 V | 5.0 V | 3.0 V | 3.0 V |
| $V_B$ | — | — | 3.0 V | 3.0 V |
| $I_D$ (dark) | ~20 nA | ~17.4 µA | ~8.3 µA | ~8.1 µA |
| $I_D$ (light) | ~110 nA | ~18.5 µA | ~6.0 µA | ~6.4 µA |
| $I_B$ (dark) | — | — | −7~−25 nA | −55~−68 nA |
| $I_B$ (light) | — | — | 40~50 nA | 28~35 nA |
| $|\Delta I_D|$ | −90 nA | ~1.1 µA | ~2.3 µA | ~1.7 µA |
| $|\Delta I_B|$ | — | — | 47~75 nA | 83~103 nA |
| $|\Delta I_D/\Delta I_B|$ | — | — | 31~49 | 17~20 |

In addition, two relevant cases have also been tabulated to gain more insights. In Case B, a larger $|\Delta I_D|$ in I-nwFET could be obtained by raising $V_D$ and $V_{Sub}$; yet, it accompanied a substantial $I_D$ increase compared with Case C (i.e., lower sensitivity). When the source and drain nanowire channels and Schottky contacts in T-nwFET had also been illuminated in Case D, the $|\Delta I_D/\Delta I_B|$ ratio was reduced versus Case C with the same terminal voltages. Without wishing to be bound by theory, this can be explained by the $R_D$ (and $R_S$) reduction which degrades the resultant $|\Delta I_D|$. Finally, the above amplification effect can be differentiated from the Schottky barrier modification mechanism (J. Zhou et al. (2009). *Appl. Phys. Lett.*, vol. 94, pp. 191 103) as the same Schottky contacts were made to the sensing nanowire in both the control I-nwFET and novel T-nwFET.

Example 4

Label-Free Prostate Specific Antigen (PSA) Detection with the Si T-nwFET Compared to a Conventional Si nwFET T-channel devices used in these studies were fabricated as described above. SEM images of the conventional nanowire and T-channel nanowire device, as well as cartoon depictions of the devices are provided in FIG. 13 and FIG. 17, respectively.

The Si nanowire surface was functionalized with 3-aminopropyltriethoxysilane (APTES) molecules to form the amino groups (—$NH_2$) (FIG. 6).

Figure 20:
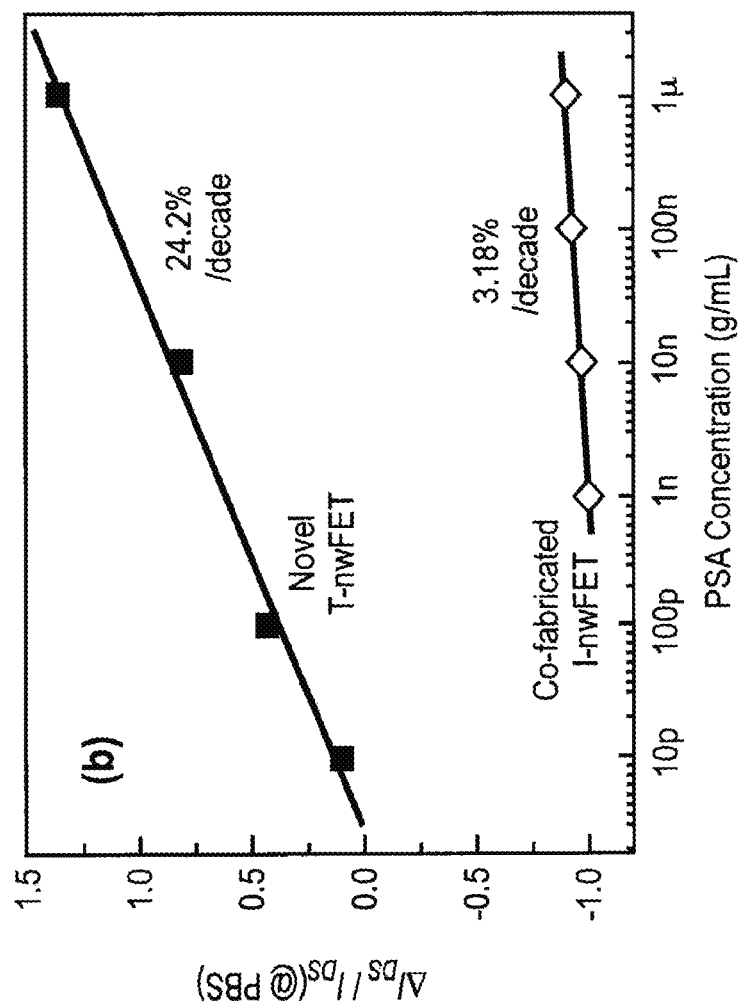
FIG. 20 is a graph showing the measured change in drain current as a function of PSA concentration.

Anti-PSA antibodies were immobilized onto the sensing nanowire surface via the APTES and glutaraldehyde linker molecules. After the introduction of PSA solutions (dissolved in phosphate buffered saline, PBS), specific antigen-antibody bindings occurred and resulted in measurable source-drain current change. As plotted in FIG. 20, the T-nwFET sensors deliver an at least 7 times higher sensitivity than the I-nwFET sensors.

Without wishing to be bound by theory, it is thought that technological improvements in nanowire fabrication should proportionally, and potentially super-linearly, enhance the T-nwFET performance.

Example 5

Detection of H1N1 and H5N1

Single and multi-channel devices for use in these studies are fabricated as described above.

PNAs (TCACTGCAAACTCATGG (SEQ ID NO: 1) and AGAAGGCCAATCCAGTC (SEQ ID NO: 2)) are synthesized for H1N1 and H5N1 respectively, as capture probes with an aldehyde on the N-terminus. These two sequences have been used previously to distinguish the binding of H1N1 and H5N1 in a microfluidic device using a large surface detection platform. The PNA probes are covalently immobilized onto the sensing nanowire surface via commercially available APTES linker molecules. The negative charge on the viral nucleic acids (e.g. RNA) can thus enable their label-free detections.

Each PNA capture probe is immobilized onto the sensing nanowire separately to detect viral target sequences for -continued (5'-ATGTAGGACCATGAGTTTGCAGTGAGTAGAAGGICACATTCTGGATTGCC-3',)
and

H5N1
SEQ ID NO: 4
(5'-GAGGTCATTGACTGGATTGGCCTTCTCCACTATGTAAGACCATTCCGGCA-3',).

Optionally, to confirm their successful immobilizations, fluorescently labeled complementary nucleic acid molecules (i.e., fluorescently labeled molecules having the sequences SEQ ID NO: 3 or SEQ ID NO: 4) are introduced onto the device, followed by confocal microscopy to visualize binding.

The two non-fluorescently labeled target sequences are mixed in different ratios to determine the detection sensitivity and specificity. A low ionic strength solution is used for the binding to the test device. The device's electrical properties are then measured. The solution is introduced either with microfluidics or manually, by a droplet or pipette.

The sensor (either the single wire or multiwire sensor) is then placed above a laboratory hot plate with good temperature control to implement the designed thermal cycle (FIG. 17, bottom). Since the wafer piece is very thermally conductive, the sensor temperature should be close to that of the hot plate surface. The temperature of the I-nwFET or T-nwFET sensing nanowire is then calibrated (with a droplet of buffer solution atop) against the hot plate reading by measuring the temperature-dependent I-nwFET or T-nwFET leakage current.

Next, viral RNA target sequences for H1N1 and H5N1, for example the sequences provided above, are introduced onto the device. Each target molecule is fully complementary to its specific binding partner. Additionally, viral RNA sequences having at least one or two mismatches are introduced to form a non-perfect binding pair. The sensor current is monitored during the RNA buffer solution introduction and the subsequent temperature ramp like in FIG. 17 (top). It is expected that a current drop will occur at $T_{m1}$ with the mere presence of mismatched RNAs in the buffer solution. A similar change should otherwise happen at $T_{m2}$ with only fully complementary RNAs. Thus, the mismatched and complementary RNAs are mixed into the same buffer solution at a different ratio to determine the sensitivity and specificity of the viral assay.

Next, the nanowire is heated to slightly above $T_{m2}$, followed by a regeneration washing step with detergent. The sensor current is monitored for any bounce-backs or $I_{blank}$, level shift.

All, document, patents, patent applications, publications, product descriptions, and protocols which are cited throughout this application are incorporated herein by reference in their entireties for all purposes.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

The invention claimed is:

1. A multiwire nanowire field effect transistor (nwFET) device comprising (a) a source electrode, (b) a drain electrode, (c) a base electrode, (d) a first nanowire having a first terminal end and a second terminal end and (e) a second nanowire having a first terminal end and a second terminal end, wherein the first nanowire and the second nanowire each comprise at least one semiconductor material, the first terminal end of the first nanowire is connected to and contacts the second nanowire to form a node, the first terminal end of the second nanowire is connected to and contacts the source electrode, the second terminal end of the second nanowire is connected to and contacts the drain electrode, and the second terminal end of the first nanowire is connected to and contacts the base electrode,
wherein the second nanowire is passivated,
wherein the first nanowire includes a sensing surface that is derivatized with a plurality of immobilized capture probes, and the sensing surface is devoid of passivation.

2. The nwFET device of claim 1, wherein the first terminal end of the first nanowire is connected to and contacts the second nanowire at an angle between about 10° and 170° to form the node.

3. The nwFET device of claim 1, wherein the at least one semiconductor material is selected from the group consisting of a group IV semiconductor material, a group III-V semiconductor material, a group II-VI semiconductor material, a group I-VII semiconductor material, a group IV-VI semiconductor material, a group V-VI semiconductor material, a group II-V semiconductor material, oxides, organic semiconductor material and a layered semiconductor material.

4. The nwFET device of claim 3, wherein the semiconductor material is silicon.

5. The nwFET device of claim 1, wherein the first nanowire is orthogonal to the second nanowire.

6. The nwFET device of claim 1, wherein the first nanowire and the second nanowire have about the same dimensions.

7. The nwFET device of claim 1, wherein a width of the first nanowire and the second nanowire are independently each within the range of about 10 nm to about 3000 nm, or within the range of about 50 nm to about 1000 nm, or within the range of about 100 nm to about 500 nm.

8. The nwFET device of claim 1, wherein a width of the first nanowire and the second nanowire are independently selected from the group consisting of about 10 nm, about 25 nm, about 50 nm, about 75 nm, about 100 nm, about 150 nm, about 200 nm, about 250 nm, about 300 nm, about 350 nm, about 400 nm, about 450 nm, about 500 nm, about 1000 nm, about 2000 nm and about 3000 nm.

9. The nwFET device of claim 1, wherein a length of the first nanowire and the second nanowire are independently selected from the group consisting of about 50 nm, about 60 nm, about 70 nm, about 80 nm, about 90 nm, about 100 nm, about 110 nm, about 120 nm, about 150 nm, about 200 nm, about 500 nm, about 1 μm, about 2 μm, about 3 μm, about 4 μm, about 5 μm, about 10 μm, about 20 μm and about 30 μm.

10. The nwFET device of claim 1, wherein each electrode is fabricated from a metal, metal alloy, metal oxide, metal nitride or conducting polymer.

11. The nwFET device of claim 2, wherein the semiconductor material is initially present as a semiconductor substrate.

12. The nwFET device of claim 11, wherein the semiconductor substrate comprises a silicon layer and a buried oxide layer.

13. The nwFET device of claim 1, wherein the immobilized capture probes comprise free amino groups, free carboxyl groups, free hydroxyl groups, or a combination thereof.

14. The nwFET device of claim 1, wherein the first nanowire is derivatized with a plurality of oligonucleotide capture probes.

15. The nwFET device of claim 1, comprising a third nanowire having a first terminal end and a second terminal end, wherein the first terminal end of the third nanowire is connected to and contacts the second nanowire to form a node, and the second terminal end of the third nanowire is connected to a second base electrode.

16. The nwFET device of claim 1, wherein the plurality of immobilized capture probes bind one or more oligonucleotides, proteins, peptides, antigens, antibodies, or fragments thereof.

17. The nwFET device of claim 1, wherein the immobilized capture probes are homogeneous for a specific target.

18. The nwFET device of claim 1, wherein the immobilized capture probes are heterogeneous for at least two targets, at least three targets, or at least four targets.

19. The nwFET device of claim 14, wherein sequences of the oligonucleotide probes are specific for RNA or DNA.

20. The nwFET device of claim 19, wherein the RNA is influenza RNA.

21. A method for detecting a change in pH in a sample, comprising:
measuring a baseline drain current ($I_D$) associated with the device of claim 1;
introducing a test sample onto the nwFET device of claim 1, wherein the first nanowire of the device is derivatized with free amino groups; and
measuring a change in $I_D$ after introduction of the sample, wherein the change in $I_D$ is associated with a change in pH of the test sample.

22. The method of claim 21, wherein the sample is an electrolyte solution or a physiological sample.

23. The method of claim 21, wherein the physiological sample is a blood sample.

24. A method for detecting the presence or absence of a molecule in a sample, comprising:
determining a baseline drain current ($I_D$) associated with the device of claim 1;
introducing a test sample onto the nwFET device of claim 1, wherein the first nanowire of the device is derivatized with immobilized capture probes specific for an analyte of interest; and measuring the $I_D$ after introduction of the sample, wherein a change in $I_D$ from baseline is associated with the analyte of interest binding the device.

25. The method of claim 24, wherein the sample is an electrolyte solution or a physiological sample.

26. The method of claim 25, wherein the physiological sample is a blood sample.

27. The method of claim 24, wherein the analyte of interest is influenza RNA or prostate specific antigen (PSA).

28. A plurality of nwFET devices of claim 1, connected in series.

29. The device of claim 15, further comprising a fourth nanowire having a first terminal end and a second terminal end, wherein the first terminal end of the fourth nanowire is connected to and contacts the second nanowire to form a node, and the second terminal end of the fourth nanowire is connected to a third base electrode.

30. The device of claim 15, wherein the first nanowire and the third nanowire are connected to the second nanowire at the same node.

31. The nwFET device of claim 1, wherein the first nanowire and the second nanowire are a monolithic structure.

* * * * *